United States Patent [19]

Theeuwes

[11] 4,111,202
[45] Sep. 5, 1978

[54] OSMOTIC SYSTEM FOR THE CONTROLLED AND DELIVERY OF AGENT OVER TIME

[75] Inventor: Felix Theeuwes, Los Altos, Calif.

[73] Assignee: Alza Corporation, Palo Alto, Calif.

[21] Appl. No.: 743,975

[22] Filed: Nov. 22, 1976

[51] Int. Cl.² .......................................... A61M 31/00
[52] U.S. Cl. ................................... 128/260; 206/0.5; 222/130; 222/193; 222/389; 222/395; 222/491; 424/19
[58] Field of Search ............... 128/260, 261, 268, 272; 424/15, 19–22, 33, 37; 222/491, 395; 206/0.5; 222/193, 389, 130

[56] References Cited

U.S. PATENT DOCUMENTS

| | | | |
|---|---|---|---|
| 3,247,066 | 4/1966 | Milosovich, Jr. | 128/260 |
| 3,732,865 | 5/1973 | Higuchi et al. | 128/260 |
| 3,760,805 | 9/1973 | Higuchi | 128/260 |
| 3,760,984 | 9/1973 | Theeuwes | 128/260 |
| 3,828,777 | 8/1974 | Ness | 128/260 |
| 3,916,899 | 11/1975 | Theeuwes et al. | 128/260 |
| 3,948,254 | 4/1976 | Zaffaroni | 128/260 |
| 3,952,741 | 4/1976 | Baker | 128/260 |
| 3,977,404 | 8/1976 | Theeuwes | 128/260 |
| 3,993,073 | 11/1976 | Zaffaroni | 128/260 |
| 4,008,719 | 2/1977 | Theeuwes et al. | 128/260 |
| 4,014,334 | 3/1977 | Theeuwes et al. | 128/260 |
| 4,016,880 | 4/1977 | Theeuwes et al. | 128/260 |
| 4,036,227 | 7/1977 | Zaffaroni et al. | 128/260 |
| 4,036,228 | 7/1977 | Theeuwes | 128/260 |

*Primary Examiner*—Benjamin R. Padgett
*Assistant Examiner*—T. S. Gron
*Attorney, Agent, or Firm*—Paul L. Sabatine; Thomas E. Ciotti; Edward L. Mandell

[57] ABSTRACT

An osmotic system for delivering a beneficial agent is disclosed. The system comprises a wall surrounding an agent compartment and an osmagent compartment separated by a film and has a passageway through the wall for delivering agent from its compartment. The wall is formed of a material permeable to the passage of an external fluid and impermeable to the passage of agent and osmagent. The film is formed of a material impermeable to the passage of agent and osmagent and movable from an original to an expanded state. The agent compartment contains an agent that is soluble in the fluid and exhibits an osmotic pressure gradient across the wall against the fluid, or the compartment contains an agent that has limited solubility in the fluid and exhibits a limited osmotic pressure gradient across the wall against fluid. The osmagent compartment contains an osmagent that exhibits an osmotic pressure gradient across the wall against the fluid. In operation, agent is delivered from the system through the passageway by fluid being imbibed through the wall into the osmagent compartment urging it to increase in volume and expand the film and correspondingly diminishing the volume of the agent compartment, whereby agent is released at a rate controlled by the permeability of the wall, the osmotic pressure gradient across the wall, and the expansion of the film over a prolonged period of time.

26 Claims, 20 Drawing Figures

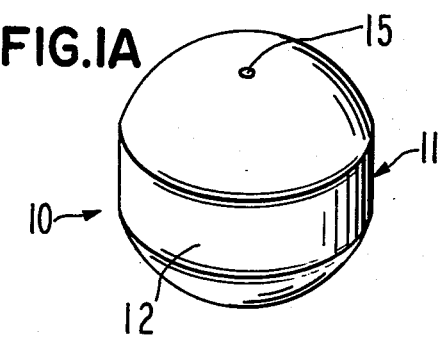
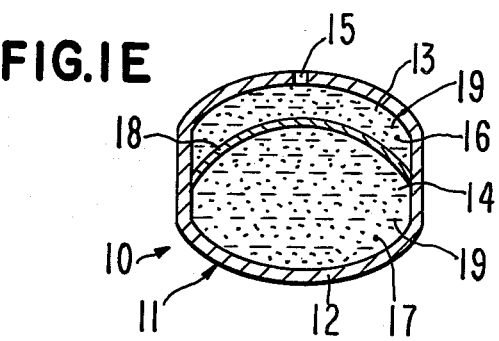
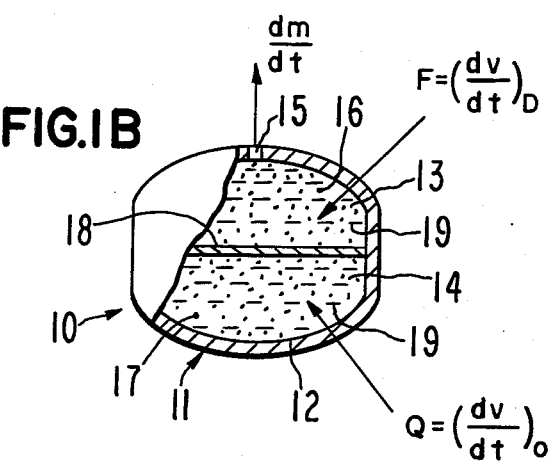
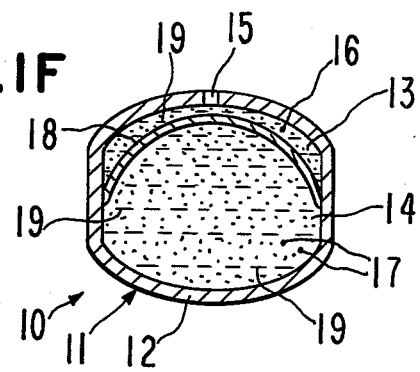
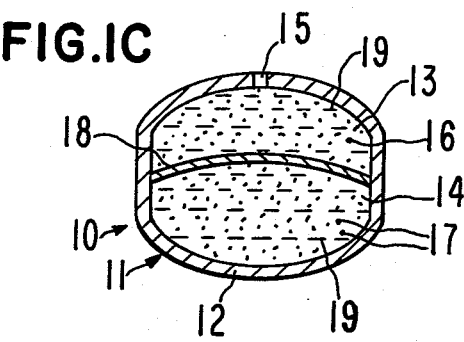
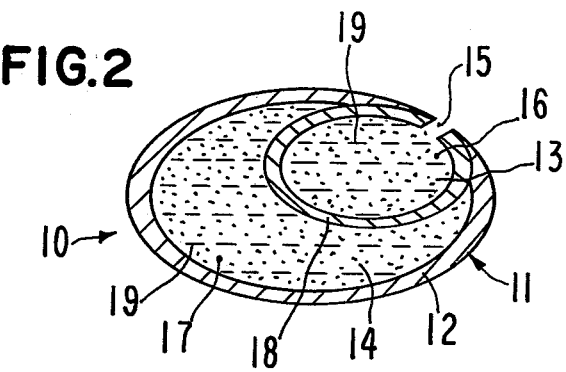
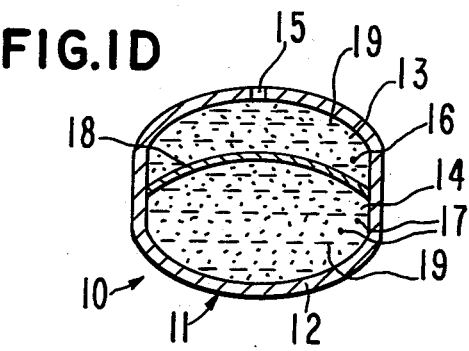
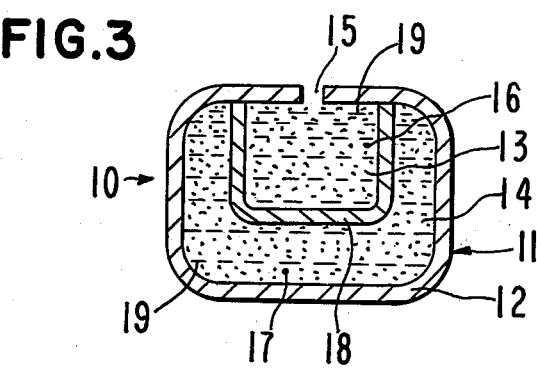

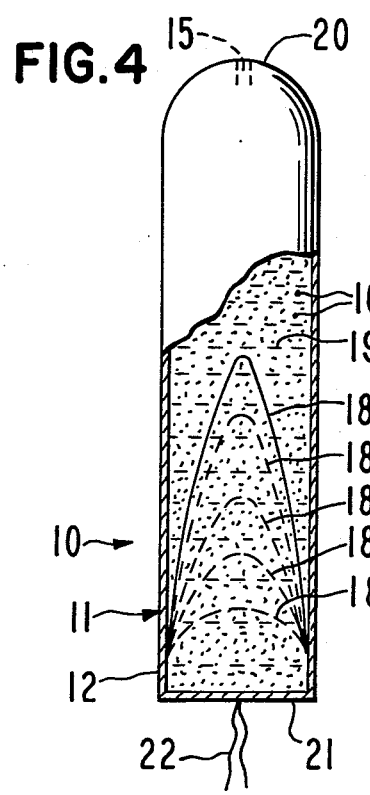
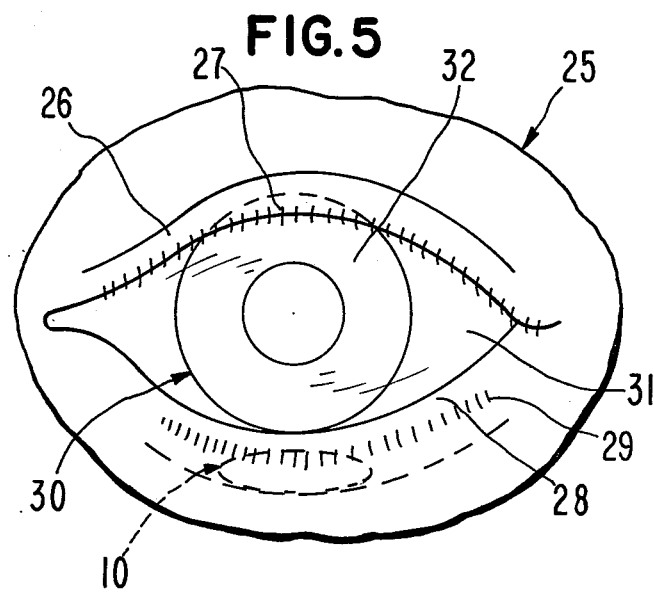
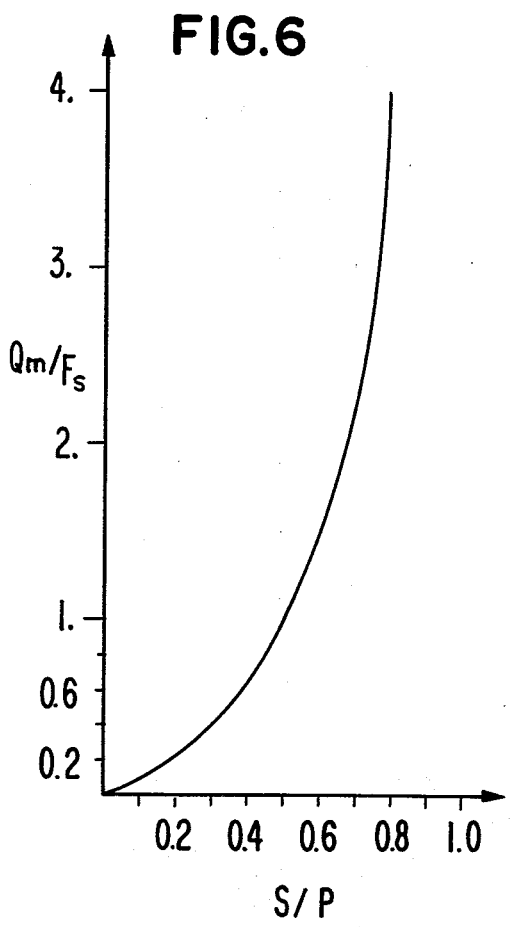
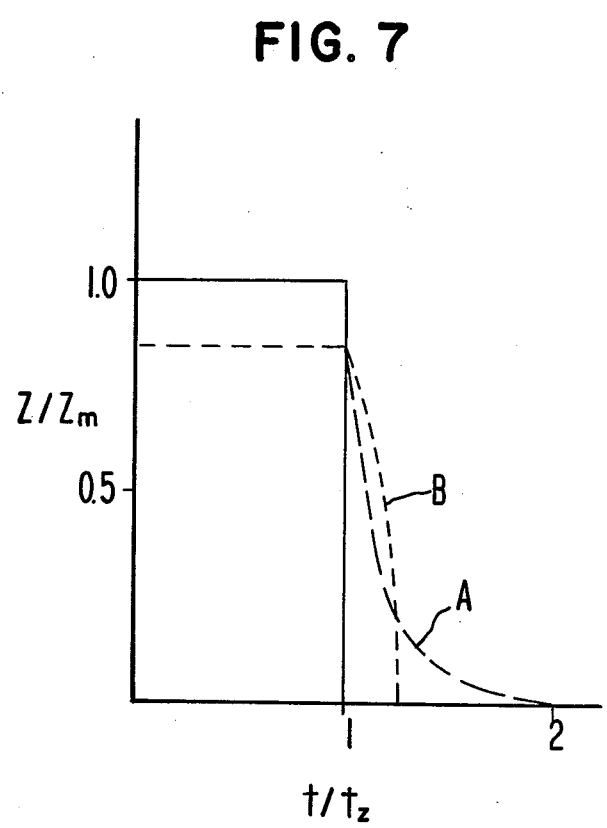

OSMOTIC SYSTEM FOR THE CONTROLLED AND DELIVERY OF AGENT OVER TIME

FIELD OF THE INVENTION

This invention pertains to an osmotic system. More particularly, the invention relates to an osmotic system manufactured in the form of an osmotic device. The system comprises a semipermeable wall surrounding a beneficial agent compartment and an osmagent compartment separated from each other by an expandable film. The osmagent compartment can increase its volume while correspondingly diminishing the volume of the agent compartment, thereby improving the delivery kinetics of the system and the amount of agent released from the system over a prolonged period of time.

BACKGROUND OF THE INVENTION

Osmotic systems manufactured in the form of osmotic devices for delivering a beneficial agent to an environment of use are known to the art in U.S. Pat. Nos. 3,845,770 and 3,916,899. The systems disclosed in these patents comprise a semipermeable wall that surrounds a compartment containing an agent. The wall is permeable to an external fluid, substantially impermeable to agent, and thee is a passageway through the wall for delivering the agent from the system. These systems release agent by fluid being imbibed through the wall into the compartment at a rate determined by the permeability of the wall and the osmotic pressure gradient across the wall to produce a solution of soluble agent, or a solution of an osmotic attractant containing insoluble agent which solution in either operation is dispensed from the system. These systems are extraordinarily effective for delivering both an agent that is soluble in the fluid and exhibits an osmotic pressure gradient across the wall against the fluid, and for delivering an agent that has limited solubility in the fluid and is admixed with an osmotically effective compound that is soluble in the fluid and exhibits an osmotic pressure gradient across the wall against the fluid. While the above systems are outstanding and represent a pioneer advancement in the delivery art, and while they are endowed with ideal delivery kinetics useful for delivering numerous beneficial agents at a controlled and continuous rate to environments of use, there is an occassional instance where the delivery kinetics of the system can be unexpectedly improved to lead to more desirable results. For example, the rate of agent delivered by the system is constant for most agents as long as excess solid agnt is present in the system with its rate declining parabolically towards zero as the agent's concentration decreases below saturation. That is, both the solubility and the density of the agent influence the amount of agent delivered at a constant rate, and that amount delivered at a declining rate is proportional to the solubility of the agent and inversely proportional to its density. These actions often make it difficult to utilize the full specific therapeutic effect of an agent, particularly when the agent is very soluble in the fluid and concomitantly a portion of the agent cannot be delivered at a constant rate over a prolonged period of time, and when the agent has limited solubility in the fluid. These latter agents do not readily form solutions or suspensions with the fluid and they exhibit limited osmotic pressure gradients across the wall, which properties make it difficult to dispense them for utilizing their full therapeutic effect. The prior art improved the delivery kinetics for both of these agents by mixing with the agents an osmagent that is coadministered with the agent. Additional prior art osmotic devices are seen in U.S. Pat. No. 3,760,804. This patent discloses a device having a rigid housing member formed of an impermeable material and having a movable separation therein forming two chambers. While this device operates successfully for its intended purpose, its use is limited because the agent must be in a semi-solid form, movable separators are hard to make and leaks often occur at the separation between the compartments. In U.S. Pat. No. 3,760,805, an osmotic device is disclosed consisting of a rigid housing member containing two bags. One bag is made of an impervious material housing a solution, semi-solid, gel or paste containing an agent, and the other bag is made of a permeable material housing an osmotic solute. While this device represents an advancement in the art, its use is limited because the agent must be in a liquid-like state. This precludes high agent loading because the liquid occupies space in the bag. Also, solid agents cannot be delivered from the device because the wall of the bag housing the agent is impermeable to the passage of fluid, which structural feature prevents both inhibition of fluid and mixing of the solid agent with fluid. The fluid is needed as a carrier for delivering agent in solution or suspension from the system. In U.S. Pat. No. 3,760,809 there is disclosed an osmotic device formed of two helical compartments consisting of one formed of an impermeable material separated by a sliding barrier plug from a second helical compartment. Also, U.S. Pat. No. 3,929,132 discloses an osmotic device made of a rigid housing member having a removable dispensing head, a threaded end, an internal agent chamber made with impermeable walls, an osmotic solute chamber having a porous membrane support for a semipermeable membrane, with the chambers separated by a movable barrier. The device of this patent operates in a manner similar to the device of U.S. Pat. No. 3,760,804 and has the same limitations. The present invention improves the delivery kinetics of the system and increases the amount of agent delivered therefrom by using an agent chamber formed with a semipermeable wall thereby making possible the housing of larger amounts, the mixing, and the delivery of solid agent from the system. The invention also uses the osmagent in a separate chamber for delivery of substantially pure agent from the system. A mathematical presentation pertaining to the instant subject matter is known in *J. Pharm. Sci.*, Vol. 64, No. 12, pages 1987 to 1991, 1975.

OBJECTS OF THE INVENTION

Accordingly, it is an immediate object of this invention to provide an improved osmotic system for the controlled and continuous delivery of a beneficial agent over a prolonged period of time which system improves the systems known to the prior art.

Yet another object of the invention is to provide an osmotic system having an agent compartment and a separate compartment that operates to diminish the volume of the agent compartment, thereby maintaining the solution in the agent compartment saturated with agent for its release over time.

Still another object of the invention is to provide an osmotic system having a compartment that continuously increases in volume while correspondingly diminishing the volume of an adjacent agent compartment for maintaining excess solid agent in solution for its constant release over time.

Still a further object of the invention is to provide an osmotic system that can continuously maintain substantially the major amount of agent present in a saturated solution with excess solid dispersed therein through the agent's release from the system.

Yet still a further object of the invention is to provide an osmotic therapeutic system that can administer a complete pharmaceutical regimen comprising very soluble or limited soluble agents at a controlled and continuous rate to animals including humans, for a particular time period, the use of which requires intervention only for initiation and possibly termination of the regimen.

Yet still another object of the invention is to provide an osmotic system having a compartment, containing the agent, which imbibes fluid osmotically, thereby formulating the agent in semi-solid form to be dispensed at a rate controlled by the osmagent compartment.

Yet still another object of the invention is to provide an osmotic system having a comaprtment containing the agent in a base which melts in the environment of use such that the agent is dispensed from the system in the base by osmotic imbibition of the osmagent compartment.

Other objects, features, aspects and advantages of the invention will be more apparent to those versed in the art from the following detailed specification, taken in conjunction with the figures and the accompanying claims.

SUMMARY OF THE INVENTION

This invention concerns an osmotic system for dispensing an active agent to a environment of use. The system comprises a semipermeable wall surrounding two adjoining compartments and has a passageway through the wall communicating with one of the compartments and the exterior of the system. The compartment with the passageway contains an agent that is soluble in an external fluid and exhibits an osmotic pressure gradient across the wall against the fluid, or it contains an agent having limited solubility in the fluid and exhibits a limited osmotic pressure gradient across the wall against the fluid. The other compartment contains a compound that is soluble in the fluid and exhibits an osmotic pressure gradient across the wall against the fluid. The compartments are separated by a contiguous film formed as a wall of one of the compartments and made of a material impermeable to agent and compound that can expand from a rested to an expanded state. Agent is released from the system by the combined action of fluid being imbibed through the wall into the compartment containing agent to product a solution, suspension, or paste containing agent, and by fluid being imbibed through the wall into the compartment containing compound causing it to increase in volume and expand, thereby exerting a force on the film urging it to expand into the adjacent compartment and diminish its volume, whereby agent is released at a rate controlled by the permeability of the wall and the osmotic pressure gradient across the wall and the expansion of the film over a prolonged period of time.

BRIEF DESCRIPTION OF THE DRAWINGS

In the drawings, which are not drawn to scale, but are set forth to illustrate various embodiments of the invention, the figures are as follows:

FIG. 1A is an isometric view of an osmotic system designed for orally administering a beneficial agent;

FIGS. 1B through 1F are side views, partially broken away, of the osmotic system of FIG. 1A illustrating the compartments of the system separated by an integrally formed contiguous expandable film;

FIG. 2 is another osmotic system seen in cross-section showing a system having two integrally formed compartments;

FIG. 3 is an osmotic system similar to FIG. 2 seen in cross-section illustrating a system embracing another design and shaped according to the invention;

FIG. 4 shows an osmotic therapeutic system designed for releasing drug in the vaginal cavity;

FIG. 5 is a front view of the human eye illustrating an osmotic therapeutic system in operative position in the environment of use;

FIG. 6 is a graph indicating the maximum desired volume flux $Q_M$ that can be designed for a osmagent compartment serving an osmotic system delivering an agent characterized by $S/\rho$ at a volume flux $F_S$;

FIG. 7 is the delivery rate from an osmotic system as a function of time;

In the drawings and specification, like parts in related figures are identified by like numbers. The terms appearing earlier in the specification and in the description of the drawings, as well as embodiments thereof, are further detailed elsewhere in the disclosure.

DETAILED DESCRIPTION OF THE DRAWINGS

Figure 8:
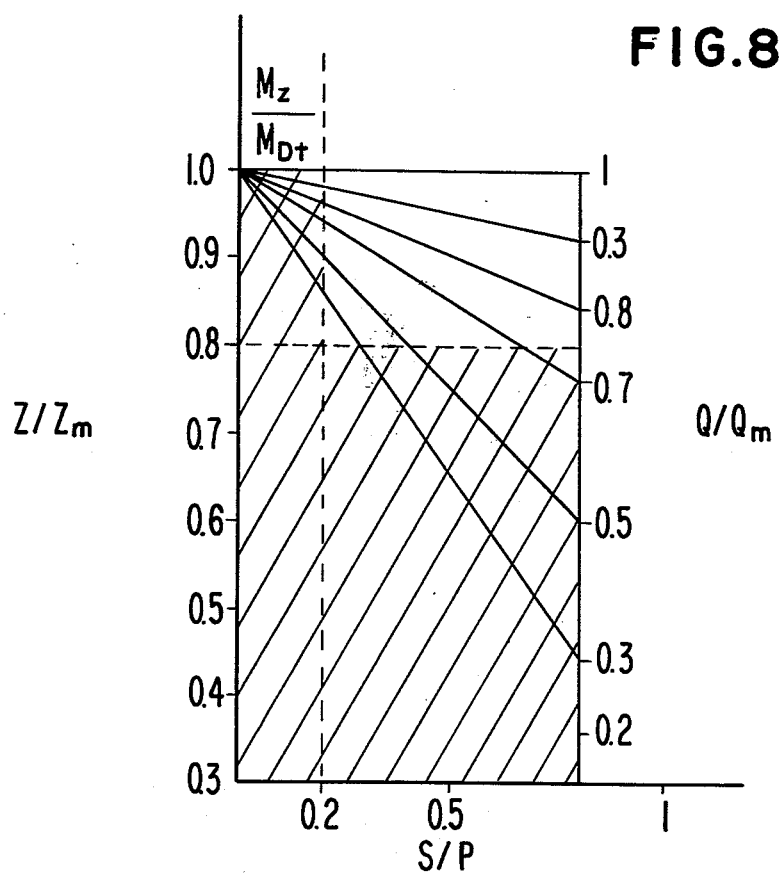
FIG. 8 is a graph depicting the zero order rate of release from the osmotic system as a function of the properties of the agents $S/\rho$ at constant values of the volume flux into the osmagent compartment.

Turning now to the drawings in detail, which are examples of various osmotic delivery systems of the invention, and which examples are not to be considered as limiting, one example of an osmotic delivery system manufactured in the form of an osmotic device is indicated in FIGS. 1A through 1F, considered together, by the numeral 10. The phrases "osmotic delivery system" and "osmotic delivery system in the form of an osmotic device" as used for the purpose of this invention, are used as functional equivalents and they also embrace the expressions "osmotic therapeutic system", "osmotic device", and "system".

In FIGS. 1A through 1F, system 10 is seen comprised of a body 11 having a wall 12 that surrounds and forms a first compartment 13 and a second compartment 14, illustrated in FIGS. 1B through 1F in crosssection, and a passageway 15 that communicates with compartment 13 and the exterior of system 10. Compartment 13, as seen in FIG. 1B, in one embodiment contains an agent 16 that is soluble to very soluble in an external fluid 19, exhibits an osmotic pressure gradient across wall 12 against the fluid and is in direct communication with wall 12, or compartment 13 in another embodiment contains an agent 16 that has limited solubility or is substantially insoluble in fluid 19 and exhibits a limited, or it not exhibit any, osmotic pressure gradient across wall 12 against the fluid, and is in contact with the interior surface of semipermeable wall 12. When agent 16 has limited solubility or it is substantially insoluble in fluid 19, it can be mixed with an osmagent that is soluble in the external fluid and exhibits an osmotic pressure gradient across wall 12 against the fluid.

Compartment 14, as seen in FIG. 1B, in a prsently preferred embodiment contains an osmagent 17, which is an osmotically effective compound, that is soluble in fluid 19 and exhibits an osmotic pressure gradient across wall 12 against fluid 19, or compartment 14 can contain a plurality of osmagents 17 with each exhibiting the same or different osmotic pressure gradients across wall 12 against fluid 19.

Compartments 13 and 14 of system 10 are separated by a contiguous film or membrane 18, seen in FIGS. 1B through 1F, for improving and assisting in regulating delivery and the amount of agent 16 from compartment 13. Film 18 is free of passageways and it is formed of an expandable material that can move from an initial or rested position, seen in FIG. 1B, through a series of sequential changes as seen in FIGS. 1C through 1E, to form fully expanded film 18 as seen in FIG. 1F.

Compartment 14 operates in cooperation with system 10, particularly compartment 13, to release agent 16 to the environment of use from system 10. System 10 in one embodiment, releases agent 16 in compartment 13 and soluble in the external fluid by fluid being imbibed into compartment 13 in a tendency towards osmotic equilibrium at a rate controlled by the permeability of wall 12 and the osmotic pressure gradient across wall 12 to dissolve agent 16 which is osmotically pumped from system 10 through passageway 15 over a prolonged period of time. Compartment 14 operates to substantially insure that delivery of agent 16 from compartment 13 is constant over a prolonged period of time by two methods. First, compartment 14 operates to continuously concentrate agent 16 by imbibing fluid from compartment 13 through film 18 to keep the concentration of agent 16 from falling below saturation. Secondly, compartment 14 by imbibing external fluid 19 across wall 12 continuously increases its volume, thereby exerting a force on film 18 urging it to expand into and diminish the volume of compartment 13, thusly insuring continuous saturation of agent 16 in compartment 13. FIGS. 1C through 1F illustrate the expansion of film 18 with the accompanying increase in volume of compartment 14 along with the simultaneous, corresponding reduction in volume of compartment 13. Compartment 13 in a presently preferred embodiment, can contain various amounts of agent 16. Agent 16 can be present in large amounts as a solid, which is mixed with fluid imbibed into compartment 13 to form a solution or suspension for release from system 10. In this manner, compartment 13 operates as a formulation compartment and thereby makes possible (a) the housing of large amounts of agent and (b) increases the amount of agent delivered at a controlled rate from system 10. System 10, in another embodiment, releases agent 16 that has limited solubility in the fluid and is mixed with an osmagent by fluid being imbibed through wall 12 into compartment 13 in a tendency towards osmotic equilibrium at a rate controlled by the permeability of wall 12 and the osmotic pressure gradient across wall 12 to continuously dissolve the osmagent and form a solution containing agent 16 that is pumped from system 10 through passageway 15. In this embodiment, compartment 14 operates as described supra. In other embodiments, agent 16 can be present as a gel, paste or semi-solid which formulation is released by the compartments of the system operating as a unit system as described above. A detailed mathematical presentation of the operation of system 10 including compartment 13 and compartment 14, appears later in the specification.

Wall 12 of system 10 is comprised of a semipermeable material that is permeable to the passage of an external fluid and it is essentially impermeable to agent 16, osmagent 17, and other ingredients housed in compartments 13 and 14. Film 18 of system 10 is formed of a material that is deformable, either permeable or impermeable to the passage of fluid, and in both instances, impermeable to the passage of agent and osmagent; and, it can undergo expansion over a prolonged period of time. Wall 12 and film 18 can be formed of synthetic or naturally occurring materials and a detailed description of these materials appears later in the specification.

System 10 of FIGS. 1A through 1F can be made into many embodiments including the presently preferred embodiments for oral use, that is, for releasing either a locally or systemically acting therapeutic agent in the gastrointestinal tract over a prolonged period of time. Oral system 10 can have various conventional shapes and sizes such as round with a diameter of 3/16 inch to ½ inch, or it can be shaped like a capsule having a range of sizes from triple zero to zero, and from 1 to 8. In these forms, system 10 can be adapted for administering agent to numerous animals, warm blooded mammals, avians and fishes.

FIGS. 2 and 3 represent additional embodiments of system 10 manufactured according to the invention and designed for dispensing agent 16 to numerous environments of use. In FIGS. 2 and 3, system 10 is seen in opened section and it is similar to system 10 of FIGS. 1A through 1F, with each system comprising a body 11 having a wall 12 that surrounds an agent compartment 13 and an osmagent compartment 14, with compartment 13 having a passageway 15 that communicates with the exterior of system 10. Compartments 13 and 14 both house the ingredients housed in FIGS. 1A through 1F. In FIGS. 2 and 3, compartments 13 and 14 are separated by movable film 18 that forms the entire barrier member between the compartments. System 10 of FIGS. 2 and 3 operate as described above with the added embodiment that all of film 18 can be used for increasing the volume of compartment 14, and that all of film 18 can be used for decreasing the volume of compartment 13, thereby insuring the controlled, continuous and constant release of agent 16 from compartment 13 to the exterior of system 10.

FIG. 4 shows an osmotic system 10 designed for placement in a vagina. System 10 has an elongated, cylindrical, self-sustaining shape with a rounded lead end 20, a trailing end 21, and it is equipped with a manually controlled cord 22 for easily removing system 10 from a vagina. System 10 is structurally identical with system 10 as described above and it has a film 18 that operates in a like manner by being capable of expanding from 18a through 18e. System 10 of FIG. 4 in one embodiment contains a drug 16 designed for absorption by the vaginal mucosa to produce a local or systemic effect, and in another embodiment it contains an odor reductant that emits an odor counteracting scent or fragrence in the vagina.

Referring to FIG. 5, an ocular therapeutic system 10 is seen in an eye 25 for administering drug at an osmotically metered dosage rate thereto. In FIG. 5, eye 25 is comprised of an upper eyelid 26 with eyelashes 27 and lower eyelid 28 with eyelashes 29. Eye 25 anatomically is comprised of an eyeball 30 covered for the greater part by sclera 31 and at its center area by cornea 32. Eyelids 26 and 28 are lined with an epithelial membrane or palpebral conjunctiva, and sclera 31 is lined with a bulbar conjunctiva that covers the exposed surface of eyeball 30. Cornea 30 is covered with a transparent epithelial membrane. The portion of the palpebral conjunctiva which lines upper eyelid 26 and the underlying portion of the bulbar conjunctiva defines an upper cul-de-sac, while that portion of the palpebral conjunctiva which lines lower eyelid 28 and the underlying portion of the bulbar conjunctiva defines a lower cul-de-sac. Ocular osmotic system 10, seen in broken lines, is designed for placement in the upper or lower cul-de-sac. System 10 is seen in the lower cul-de-sac and it is held in place by the natural pressure of lower eyelid 28. System 10 contains an ophthalmic drug for release to eye 25 at a controlled and continuous rate over a prolonged period of time.

Ocular system 10, manufactured according to the inventive principles described supra, can have any geometric shape that fits comfortably in the cul-de-sac. Typical shapes include, ellipsoid, bean, banana, circular, ring, rectangular, doughnut, crescent and half-ring shaped systems. In cross-section, the systems can be doubly convex, concavo-convex, rectangular and the like, as the device in use will tend to conform to the shape of the eye. The dimensions of an ocular system can vary widely with the lower limit governed by the amount of drug to be administered to the eye as well as the smallest sized system that can be placed into the eye. The upper limit on the size of the system is governed by the space limitation in the eye consistent with comfortable retention in the eye. Satisfactory systems have a length of 4 to 20 millimeters, a width of 1 to 15 millimeters. The ocular system can contain from 0.15 micrograms to 100 milligrams of drug, or more, and it is made from materials non-toxic to the eye.

While FIGS. 1 through 5 are illustrative of various systems that can be made according to the invention, it is to be understood these systems are not to be construed as limited, as the system can take a wide variety of shapes, sizes and forms for delivering agent to different environments of use. For example, the system includes buccal, implant, anal, rectal, artificial gland, cervical, intrauterine, ear, nose, dermal, subcutaneous, and blood systems. The systems also can be sized, shaped and adapted for delivering an active agent in streams, aquariums, fields, factories, reservoirs, laboratory facilities, hot houses, transportation means, naval means, military means, hospitals, veterinary clinics, nursing homes, farms, zoos, sickrooms, chemical reactions, and other environments of use.

DETAILED DESCRIPTION OF THE INVENTION

In accordance with the practice of the invention, it has now been found that osmotic delivery system 10 can be manufactured with a wall 12 formed of a material that does not adversely affect the agent and osmagent, an animal body, or other host, and is permeable to an external fluid 16 such as water and biological fluids while remaining essentially impermeable to agents, including drugs, osmagents, and the like. The selectively permeable materials forming wall 12 are insoluble in body fluids, and they are non-erodible, or they can be made to bioerode after a predetermined period with bioerosion corresponding to the end of the agent release period. Typical materials for forming wall 12 include semipermeable materials known to the art as osmosis and reverse osmosis membranes such as cellulose acetate, cellulose triacetate, agar acetate, amylose triacetate, beta glucan acetate, cellulose diacetate, acetaldehyde dimethyl acetate, cellulose acetate ethyl carbamate, polyamides, polyurethane, sulfonated polystyrenes, cellulose acetate phthalate, cellulose acetate methyl carbamate, cellulose acetate succinate, cellulose acetate dimethylaminoacetate, cellulose acetate ethyl carbamate, cellulose acetate chloroacetate, cellulose dipalmitate, cellulose dioctanoate, cellulose dicaprylate, cellulose dipentanlate, cellulose acetate valerate, cellulose acetate succinate, cellulose propionate succinate, methyl cellulose, cellulose acetate p-toluene sulfonate, cellulose acetate butyrate, selectively permeable polymers formed by the coprecipitation of a polycation and a polyanion as disclosed in U.S. Pat. Nos. 3,173,876; 3,276,586; 3,541,005; 3,541,006; and 3,546,142. Generally, semipermeable materials useful for forming wall 12 will have a fluid permeability of $10^{-5}$ to $10^{-1}$ (cc.mil/cm$^2$.hr.atm) expressed per atmosphere of hydrostatic or osmotic pressure difference across wall 12 at the temperature of use. Other suitable materials are known to the art in U.S. Pat. Nos. 3,845,770 and 3,916,899.

Film 18 of system 10, also known as membrane 18, is formed from the above materials and it is made expandable by (1) controlling its thickness to about 2 to 6 mils, and (2) by optionally adding from 0.01% to 40% of a film expansion agent that imparts flexibility, deformability and expansion properties thereto. Generally, a film expansion agent, or a multiplicity of film expansion agents are added to the material forming film 18 when the material has a moderate to high degree of substitution or a moderate to high acyl content, usually 35 to 43%. Suitable agents include polyhydric alcohols and derivatives thereof, such as polyalkylene glycols of the formula H-(O-alkylene)$_n$—OH wherein the bivalent alkylene radical is straight or branched chain and has from 1 to 10 carbon atoms and $n$ is 1 to 500 or higher. Typical glycols include polyethylene glycols 300, 400, 600, 1500, 1540, 4000 and 6000 of the formula H—(OCH$_2$CH$_2$)$_n$—OH wherein $n$ is respectively 5, 5.7, 8.2 to 9.1, 12.5 to 13.9, 29 to 36, 29.8 to 37, 68 to 84, and 158 to 204. Other polyglycols include low molecular weight glycols such as polypropylene, polybutylene and polyamylene.

The film expansion agents in another embodiment include poly($\alpha,\omega$)-alkylenediols wherein the alkylene is straight or branched chain of from 2 to 10 carbon atoms such as poly(1,3)-propanediol, poly(1,4)-butanediol, poly(1,5)-pentanediol and poly(1,6)-hexanediol. The diols also include aliphatic diols of the formula $HOC_nH_{2n}OH$ wherein $n$ is from 2 to 10 and the diols are optionally bonded to a non-terminal carbon atom such as 1,3-butylene glycol, 1,4-pentamethylene glycol, 1,5-hexamethylene glycol and 1,8-decamethylene glycol; and alkylenetriols having 3 to 6 carbons atoms such as glycerine, 1,2,3-butanetriol, 1,2,3-pentanetriol, 1,2,4-hexanetriol, 1,3,6-hexanetriol, and mixtures thereof.

Other film or membrane expanding agents include esters and polyesters of alkylene glycols of the formula $HO$—$(alkylene-O)_n$—$H$ wherein the divalent alkylene radical includes the straight chain groups and the isomeric forms thereof having from 2 to 6 carbons and $n$ is 1 to 14. The esters and polyesters are formed by reacting the glycol with either a monobasic or dibasic acid. Exemplary agents are ethylene glycol dipropionate, ethylene glycol butyrate, ethylene glycol diacetate, triethylene glycol diacetate, butylene glycol dipropionate, polyester of ethylene glycol with succinic acid, polyester of diethylene glycol with maleic acid, and polyester of triethylene glycol with adipic acid.

Exemplary film expansion agents suitable for the present purpose generically include agents that lower the temperature of the second-order phase transition of the film forming materials or the elastic modulus thereof, increase the workability of the film, its flexibility, and its permeability to fluid. Agents operable for the present purpose include both cyclic and acyclic agents. Typical agents are those selected from the group consisting of phthalates, phosphates, citrates, adipates, tartrates, sebacates, succinates, glycolates, glycerolate, benzoates, myristates, sulfonamides, and halogenated phenyls.

Exemplary film expanders further include dialkyl phthalates, dicycloalkyl phthalates, diaryl phthalates and mixed alkyl-aryl phthalates as represented by dimethyl phthalate, dipropyl phthalate, di(2-ethylhexyl)phthalate, di-isopropyl phthalate, diamyl phthalate and dicapryl phthalate, alkyl and aryl phosphates such as tributyl phosphate, trioctyl phosphate, tricresyl phosphate, trioctyl phosphate, tricresyl phosphate and triphenyl phosphates; alkyl citrate and citrate esters such as tributyl citrate, triethyl citrate, and acetyl triethyl citrate; alkyl adipates such as dioctyl adipate, diethyl adipate and di(2-methoxyethyl)-adipate; dialkyl tartrates such as diethyl tartrate and dibutyl tartrate; alkyl sebacates such as diethyl sebacate, dipropyl sebacate and dinonyl sebacate; alkyl succinates such as diethyl succinate and dibutyl succinate; alkyl glycolates, alkyl glycerolates, glycol esters and glycerol esters such as glycerol diacetate, glycerol triacetate, glycerol monolactate diacetate, methyl phthayl ethyl glycolate, butyl phthalyl butyl glycolate, ethylene glycol diacetate, ethylene glycol dibutyrate, triethylene glycol diacetate,, triethylene glycol dibutyrate and triethylene glycol dipropionate. Also, camphor, N-ethyl-(o- and p-toluene) sulfonamide, chlorinated biphenyl, benzophenone, N-cyclohexyl-p-toluene sulfonamide, and substituted epoxides.

Suitable film expansion agents can be selected for blending with the film forming materials by selecting agents that have a high degree of solvent power for the materials, are compatible with the materials over both the processing and use temperature range, exhibit permanence as seen by a strong tendency to remain in the film, impart the desired properties, and are non-toxic to animals, including humans, avians, fishes and reptiles. Procedures for selecting an agent having the described characteristics are disclosed in the *Encyclopedia of Polymer Science and Technology,* Vol. 10, pages 228 to 306, 1969, published by John Wiley & Sons, Inc.

The expression "passageway" as used herein comprises means and methods suitable for releasing the agent from the system. The expression includes aperture, orifice or bore through wall 12 formed by mechanical procedures, or by eroding an erodible element, such as gelatin plug, in the environment of use. A detailed description of osmotic passageways and the maximum and minimum dimensions for a passageway are disclosed in U.S. Pat. Nos. 3,845,770 and 3,916,899.

The osmotically effective compounds 17 that can be used for the purpose of the invention include inorganic and organic compounds that exhibit an osmotic pressure gradient against an external fluid 19 across wall 12 and film 18. These compounds are known as osmagents. The osmagents, when present in compartment 13, are mixed with an agent that has limited solubility in external fluid with the osmagent forming a saturated solution when mixed with fluid containing agent that is osmotically delivered from the system. In agent 16 is soluble in the fluid, an osmagent is not needed and pure agent can therefore be delivered from the device. The osmagents are present in compartment 14 for: (a) imbibing fluid from compartment 13 to concentrate solution in compartment 13; and (b) for compartment 14 to fill and expand in volume with a corresponding collapse of compartment 13. The osmagents are used by homogenously or heterogenously mixing them or a mixture of osmagents with agent 16, either before they are charged into compartment 13, or by self-mixing after they are charged into compartment 13. In operation, these osmagents attract fluid into compartment 13 producing a solution of osmagents which is delivered from the system concomitantly transporting undissolved and dissolved agent 16 to the exterior of the system. The osmagents are present in compartment 14 independent of the presence of any other agent. Osmotically effective compounds 16 useful for the present purpose include magnesium sulfate, magnesium chloride, sodium chloride, lithium chloride, potassium sulfate, sodium carbonate, sodium sulfite, lithium sulfate, potassium chloride, calcium carbonate, sodium sulfate, calcium sulfate, potassium acid phosphate, calcium lactate, d-mannitol, urea, inositol, magnesium succinate, tartaric acid, carbohydrates such as raffinose, succrose, glycose, and mixtures thereof. Osmagent 16 suitable for housing in compartment 14 also includes starches and carbohydrates such as algin, sodium alginate, potassium alginate, carrageenan, fucoridan, furcellaran, laminaran, hypnea, gum arabic, gum ghatti, gum karaya, locust bean gum, pectin, starch, mixtures thereof, and the like. The osmagent is usually present in an excess amount, and it can be in any physical form such as particle, crystal, pellet, tablet, strip, powder, film or granule. The osmotic pressure $\pi$ in atomospheres ATM, of the osmagents suitable for the invention will be greater than zero ATM, generally from zero ATM up to 500 ATM, or higher.

The expressions "active agent" and "beneficial agent" as used herein broadly includes any compound, composition of matter or mixture thereof, that can be delivered from the system to produce a beneficial and useful result. The agent can be soluble in fluid 19 that enters the compartment 13 and functions as its own osmotically effective solute, or it can have limited solubility in the fluid and be mixed with an osmotically effective compound 17 soluble in fluid that is delivered from the system. The active agent includes pesticides, herbicides, germicides, biocides, algicides, rodenticides, fungicides, insecticides, anti-oxidants, plant growth promoters, plant growth inhibitors, preservatives, anti-preservatives, disinfectants, sterilization agents, catalysts, chemical reactants, fermentation agents, foods, food supplements, nutrients, cosmetics, drugs, vitamins, sex sterilants, fertility inhibitors, fertility promoters, air purifiers, micro-organism attenuators, and other agents that benefit the environment of use.

In the specification and the accompanying claims, the term "drug" includes an physiologically or pharmcologically active substance that produces a localized or systemic effect or effects in animals, including warm blooded mammals, humans and primates, avians, domestic household, sport or farm animals such as sheep, goats, cattle, horses and pigs, for administering to laboratory animals such as mice, rats and guinea pigs, to fishes, reptiles zoo and wild animals. The active drug that can be delivered includes inorganic and organic compounds without limitation, those materials that act on the central nervous system such as hypnotics and sedatives, psychic energizers, tranquilizers, anticonvulsants, muscle relaxants, antiparkinson agents, analgesics, anti-inflammatory, local anesthetics, muscle contractants, anti-microbials, anti-malarials, hormonal agents including contraceptives, sympathomimetrics, diuretics, anti-parasitics, neoplastics, hypoglycemics, nutritional, fats, ophthalmic, electrolytes and diagnostic agents.

Exemplary of drugs that are soluble or very soluble in water and can be delivered by the systems of this invention include prochlorperazine edisylate, ferrous sulfate, aminocaproic acid, potassium chloride, mecamylamine hydrochloride, procainamide hydrochloride, amphetamine sulfate, benzphetamine hydrochloride, isoproternol sulfate, methamphetamine hydrochloride, phenmetrazine hydrochloride, bethanechol chloride, methacholine chloride, pilocarpine hydrochloride, atropine sulfate, methascopolamine bromide, isopropamide iodide, tridihexethyl chloride, phenformin hydrochloride, methylphenidate hydrochloride, and mixtures thereof.

Exemplary of agents that have limited solubility or are very slightly soluble, or insoluble in water and biological fluids that can be delivered by the systems of this invention include diphenidol, meclizine hydrochloride, prochlorperazine maleate, thiethylperazine maleate, anisindione, diphenadione, erythrityl tetranitrate, dizoxin, isoflurophate, reserpine, azetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, and mixtures thereof, steroids including corticosteroids such as hydrocortisone, hydrocorticosterone acetate, cortisone acetate and triamcinolone, anhydrogens such as methyltesterone, esterogenic steroids such as $17\beta$-estradiol, ethinyl estradiol, ethinyl estradiol 3-methyl ether and estradiol, progestational steroids such as prednisolone, $17\alpha$-hydroxy-progesterone acetate, 19-nor-progesteroine, norethindrone, progesterone, norethynodrel, and the like.

The drug can also be in various chemical and physical forms, such as uncharged molecules, molecular complexes, pharmacologically acceptable acid addition and base addition salts such as hydrochlorides, hydrobromides, sulfate, laurylate, palmitate, phosphate, nitrate, borate, acetate, maleate, tartrate, oleate, and salicylate. For acidic drugs, salts of metals, amines or organic cations, for example quaternary ammonium can be used. Derivatives of drugs such as ester, ethers and amides can be used alone or mixed with other drugs. Also, a drug that is water insoluble can be used in a form that on its release from the device, such as prodrug, is converted by enzymes, hydrolyzed by body pH or other metabolic processes to the original form, or to a biologically active form. Agent 16 can be in the compartment 13 as a dispersion, paste, cream, gels, particle, granule, emulsion, suspension or powder. Also, agent 16 can be mixed with a binder, dispersant, emulsifier, wetting agent or dye.

The amount of agent 16 present in the system is initially in excess of the amount that can be dissolved in or mixed with the fluid that enters the compartment. Under this physical and chemical state when the agent is in excess, the system will osmotically operate to give a substantially constant rate of release. The rate of agent release pattern can also be varied by having different amounts of agent in the compartment to form solutions or mixtures containing different concentrations of agent for delivery from the system. Generally, the system can house from 0.05 ng to 5 grams or more, with individual systems containing for example, 25 ng, 1 mg, 5 mg, 250 mg, 500 mg, 1.5 g, and the like. The beneficial drugs are known to the art in *Pharmaceutical Sciences*, by Remington, 14th Ed., 1970, published by Mack Publishing Co., Easton, Penna; *The Drug, The Nurse, The Patient, Including Current Drug Handbook*, 1974–1976, by Falconer, et al, published by Saunder Company, Philadelphia, Penna; and, *Medicinal Chemistry*, 3rd Ed., Vol. I & II, by Burger, A., published by Wiley-Interscience, New York.

The solubility or insolubility of agent 16 in an external fluid 19 can be determined by various art known techniques. One method consists in preparing a saturated solution comprising the external fluid plus the agent as ascertained by analyzing the amount present in a definite quantity of the fluid. A simple apparatus for this purpose consists of a test tube of medium size fastened upright in a water bath maintained at constant temperature and pressure, for example, one atmosphere, in which the fluid and agent are placed and stirred by a motor driven rotating glass spiral. After a given period of stirring, a definite weight of the fluid is analyzed and the stirring continued for an additional period of time. If the analysis shows no increase of dissolved agent after successive periods of stirrings, in the presence of excess solid agent in the fluid, the solution is saturated and the results are taken as the solubility of the product in the fluid. If the agent is soluble an added osmagent 17 is not needed; if the agent has limited solubility or it is insoluble in the fluid, then an osmagent 17 can optionally be incorporated into compartment 13. Numerous other methods are available for determining the solubility of an agent in a fluid. Typical methods used for measuring solubility include chemical analysis, ultra violet spectrometry, density, refractive index and electrical conductivity. Generally, for the purpose of this invention soluble to very soluble agents will dissolve in the range of from 150 mg to 900 mg of agent per milliliter of solution, and limited soluble to insoluble agents will dissolve in the range of 0.001 mg to 125 mg of agent per milliliter of fluid or less. While the invention has been described with particular reference to presently preferred embodiments including soluble and insoluble, it is understood the system of the invention can be used to deliver other agents having other kinds of solubilities.

Details of various methods for determining solubilities are described in *United States Public Health Service Bulletin*, No. 67 of the Hygienic Laboratory; *Encyclopedia of Science and Technology*, Vol. 12, pages 542 to 556, 1971, published by McGraw-Hill, Inc.; and *Encyclopedia Dictionary of Physics*, Vol. 6, pages 547 to 557, 1962, published by Pergamon Press, Inc.

The systems of the invention are manufactured by standard techniques. For example, in one embodiment, agent 16 and optionally, osmagent 17 and other ingredients that may be housed in compartment 13 and a solvent are mixed into a solid, semi-solid or pressed state by conventional methods such as ballmilling, calendering, stirring or rollmilling and then pressed or tableted into a preselected shape. The film forming compartment 13 made of a material containing a film expansion agent can be applied thereto by molding, spraying or dipping the pressed shape into the film forming material. In another embodiment, a film can be cast, shaped to the desired dimensions that surround compartment 13 that is then filled with agent 16 and closed. The system also can be manufactured with an empty compartment that is filled through the passageway. Compartment 14 is formed by pressing an osmagent 17 into a preselected shape which is then intimately attached to compartment 13. Finally, juxtaposed compartments 13 and 14 are surrounded with a semipermeable wall 12. Optionally, system 10 can be manufactured by first fabricating compartment 14 by pressing in a standard tableting machine an osmagent to form a predetermined shaped system which is then surrounded with a film forming material to form a closed compartment. Next, compartment 13 is formed by pressing an agent into a predetermined shape which pressed agent is joined to compartment 14. Finally, the two adjacent compartments are surrounded with a wall formed of a semipermeable material and a passageway is drilled through the wall into active agent compartment 13 to form osmotic system 10.

Compartments 13 and 14 as described immediately above can be joined by methods well-known to the art, or they can be integrally formed as illustrated in the above figures. One operable method for joining the compartments consists in applying a dash or thin layer of a non-toxic adhesive to the joinable surfaces immediately preceeding their alignment into a working structure. Adhesives suitable for the present purpose include semipermeable silicon glue, cellulose nitrate, cellulose acetate, vinyl acetate and vinyl chloride adhesives, acrylic resins, aldehyde resins, water soluble gums, aqueous dispersions of paraffins, monomeric esters of α-cyanoacrylic acid, ureas, and the like. These adhesives are disclosed to the art in U.S. Pat. Nos. 3,547,771; 3,552,994; 3,598,781; 3,627,559; 3,627,609; 3,755,044; and 3,759,264; in West Germany Pat. No. DT 2,009,968; and in British Pat. No. 577,735. The compartments also can be joined by other methods including heat sealing, pressing, consecutively casting the compartments in a dual cavity mold, overlaying, and the like.

The walls and films forming the system can be joined by various techniques such as high frequency electronic sealing that provides clean edges and firmly formed walls and films, and, a presently preferred technique that can be used is the air suspension procedure. This procedure consists in suspending and tumbling the agent or osmagent in a current of air and a wall forming, or film forming, composition until the wall or film is applied to the agent or osmagent. The air suspension procedure is well-suited for independently forming the walls and films. The air suspension procedure is described in U.S. Pat. No. 2,799,241; in *J. Am. Pharm. Assoc.*, Vol. 48, pages 451 to 459, 1959; and ibid., Vol. 49, pages 82 to 84, 1960. Other wall and film forming techniques such as pan coating can be used in which the materials are deposited by successive spraying of the polymer solution on the agent or osmagent accompanied by tumbling in a rotating pan. Other standard manufacturing procedures are described in *Modern Plastics Encyclopedia*, Vol. 46, pages 62 to 70, 1969; and in *Pharmaceutical Sciences*, by Remington, 14th Ed., pages 1626 to 1678, 1970, published by Mack Publishing Company, Easton, Penna.

Generally the films can be separately or integrally fabricated and will have a thickness of about 2 to 6 mils. The film can be formed with or without a film expansion agent and will have a presently preferred thickness of about 3.5 to 5.5 mils. The semipermeable walls will have a thickness of 5 to 15 mils, with a presently preferred thickness of about 7 to 12 mils. Of course, thinner and thicker films and walls for use with numerous agents and osmagents are within the scope of the invention.

Exemplary solvents suitable for manufacturing the wall, or the film include inert inorganic and organic solvents that do not adversely harm the wall forming materials, the film forming materials, and the final system. The solvents broadly include members selected from the group consisting of aqueous solvents, alcohols, ketones, esters, ethers, aliphatic hydrocarbons, halogenated solvents, cycloaliphatic aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclo-octane, benzene, toluene, naphtha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol, and mixtures thereof.

DESCRIPTION OF EXAMPLES OF THE INVENTION

The following examples are merely illustrative of the present invention and they should not be considered as limiting the scope of the invention in any way, as these examples and other equivalents thereof will become apparent to those versed in the art in the light of the present disclosure, the drawings and the accompanying claims.

EXAMPLE 1

An osmotic delivery device for the controlled and continuous release of a beneficial agent to an environment of use is constructed as follows: first, an osmagent compartment is formed by pressing and thinly encapsulating a given amount of an osmagent with a film consisting of a semipermeable material containing a film expansion agent in an air suspension machine. Next, an agent compartment is formed by compressing a water soluble agent that exhibits an osmotic pressure gradient across a wall into a shape corresponding to the shape of the osmagent compartment. Then, a thin layer of a flexible adhesive is applied to one surface of the osmagent compartment and the agent compartment juxtapositioned thereto. Next, the two compartments are surrounded with a wall of a semipermeable, polymeric wall forming material. Finally, a passageway is drilled through the wall to the agent compartment to form the osmotic system.

The system of this example is illustrated in FIG. 1B, and it releases agent at a zero order rate of release over a prolonged period of time. In FIG. 1B, the agent compartment is identified as 13, hereafter referred to as the D compartment, the osmagent compartment is identified as 14, hereafter referred to as the O compartment, with delivery from system 10, when placed in an aqueous environment, governed by the following relations. In operation, aqueous fluid is imbibed into the D compartment at a volume rate given by Relation 1:

$$F = [dV/dt]_D \qquad (1)$$

with agent release from this compartment at a mass rate given by Relation 2:

$$[dm/dt] = F \cdot C \qquad (2)$$

wherein $C$ is the concentration of agent in solution. Fluid is imbibed into O compartment at a volume rate $(dV/dt)_O$ equal to the volume change of O compartment $(dV_O/dt = O)$ pushing an equal volume of agent solution $(-dV_D/dt)$ as expressed by Relation 3 as follows:

$$[dV/dt]_O = dV_O/dt = Q = -dV_D/dt \qquad (3)$$

adding a simultaneous contribution to the delivery rate as expressed by Relation 4:

$$[dm/dt]_O = Q \cdot C \qquad (4)$$

with the total delivery rate from the system obtained from Relation 2 and 4 as given by Relation 5:

$$dm/dt = (F + Q) \cdot C \qquad (5)$$

The system is advantageously constructed for agents delivering low fractions of their agent content at zero order from the osmotic system. This invention programs $D$ compartment to formulate the agent solution at a constant concentration, $S$, with the $O$ compartment serving as the driving mechanism to deliver agent at a constant rate throughout the lifetime of the system. In a two compartment system, both compartments are driven from the same external reference solution, and a zero order rate can be maintained for a $Q$ sufficiently large to displace all the saturated agent solution. Throughout this example, the expandable film is deemed impermeable to an agent or osmagent which is correct for a semipermeable film separating isotonic solutions.

Relation 6 describes the minimum mass of osmagent $M_O$ necessary for the O compartment to exert a constant force. $V_O$ and $V_d$ are respectively the initial osmagent and drug compartment volumes:

$$[M_O]_{min} = S_O[V_O + V_D] \qquad (6)$$

The system also can be programmed with constant osmotic compartments, O compartments, applying a force, or pushing against a D compartment at different rates. An important application exists when an O compartment exerts a force, or drives, at its maximum value $Q_{max}$ equal to the rate at which agent solution is formulated in D compartment. The release rate for the application $Q = Q_{max}$ achieves its maximum value $(dm/dt)_M$ for a given agent compartment, D, and is constant throughout the total lifetime of the system. The volume rate into D compartment is a constant $F_S$ when saturated agent solution is contained in D compartment with an osmotic pressure $\pi_{DS}$ which conditions are expressed in Relation 7:

$$F_S = k_D \pi_{DS}(A_D/h_D) \qquad (7)$$

wherein $A_D$, $h_D$, and $k_D$ are respectively the wall area, thickness and water permeability of the D compartment. The maximum zero order rate of release is then obtained from Relation 8 in which S is the agent solubility:

$$[dm/dt]_{M,z} = F_S + Q_M \cdot S \qquad (8)$$

expressed as mass per volume of solution, $Q_M$ is equal to the volume of agent dissolved in the agent compartment per unit time $(dV_C/dt)$ which is related to the agent dissolution rate $dm_C/dt$ as set forth in Relation 9 wherein $\rho$ is the agent's density:

$$Q_M = \frac{dV_C}{dt} = \frac{1}{\rho} \frac{dm_C}{dt} \qquad (9)$$

Since a mass of agent, $dm_C$, dissolves in a volume, $dV_W$ of aqueous fluid, $dm_C/dV_W$ in Relation 10 expresses the solubility of the agent per unit volume of aqueous fluid, $S_W$, which is related to S by Relation 11 and $dV_W/dt$ is equal to the influx, $F_S$, into D compartment at saturation. This latter result is expressed in Relation 12. Relations 10, 11 and 12 are as follows:

$$Q_M = \frac{1}{\rho} \frac{dm_C}{dV_W} \cdot \frac{dV_W}{dt} \qquad (10)$$

$$S_W = \frac{S}{1 - \frac{S}{\rho}} \qquad (11)$$

$$Q_M = \frac{1}{\rho} \left[ \frac{S}{1 - \frac{S}{\rho}} \right] \cdot F_S \qquad (12)$$

Substituting Relation 12 into Relation 8, the maximum zero order rate of release $Z_M$ is then expressed by Relation 13 or Relation 14 as follows:

$$Z_M = \left[ \frac{dm}{dt} \right]_{M,z} = F_S \cdot \frac{S}{1 - \frac{S}{\rho}} \qquad (13)$$

$$Z_M = \rho \cdot Q_M \qquad (14)$$

In a visual comparison of Relation 9 and Relation 14, it is mathematically evident that $(dm/dt)_{M,z}$ as given by Relation 14 is equal to the rate of dissolution of agent in the agent compartment as produced by influx $F_S$. Alternatively, Relation 14 can be considered as a mass delivery rate produced by a volume flux $Q_M$ displacing a mass of agent with density $\rho$. The zero order time, $t_z$, is the time necessary to deliver the total agent content, $M_{D,t}$, as expressed in Relation 15:

$$t_z = \frac{M_{D,t}}{F_S \cdot S} \cdot \left(1 - \frac{S}{\rho}\right) \tag{15}$$

For the application where $Q < Q_{max}$, the force or pushing rate exerted by O compartment is constant but smaller than its maximum value, and under these conditions, agent will be dispensed at zero order for a time, $t_z$, followed by a declining delivery rate portion. The zero rate is given by Relation 5 expressed as Relation 16:

$$Z = \left[\frac{dm}{dt}\right]_z = (F_S + Q) \cdot S \tag{16}$$

The zero order rate, $Z$, can be calculated as a fraction of the maximum zero order rate $Z_M$ from Relation 14 and Relation 16 and expressed as Relation 17 as follows:

$$\frac{Z}{Z_M} = \left[\frac{F_S}{Q_M} + \frac{Q}{Q_M}\right]\frac{S}{\rho} \tag{17}$$

with $F_S/Q_M$ obtained from Relation 12 such that Relation 18 and Relation 19 hold as follows:

$$\frac{Z}{Z_M} = 1 - \frac{S}{\rho} + \frac{Q}{Q_M} \cdot \frac{S}{\rho} \tag{18}$$

$$\frac{Z}{Z_M} = 1 - \frac{S}{\rho}\left[1 - \frac{Q}{Q_M}\right] \tag{19}$$

and $Z/Z_M$ is a linear decreasing function of $S/\rho$ with slope $(1 - Q/Q_M)$.

The time the system delivers agent at zero order rate is the time required to deliver the mass of agent $M_Z$ which is smaller than the total mass $M_{D,t}$ as expressed by Relation 20:

$$M_Z = t_Z \cdot \left[\frac{dm}{dt}\right]_z \tag{20}$$

with the mass of agent delivered at zero order being the total mass minus the mass not delivered at zero order, or the mass dissolved in the agent compartment D at time $t_Z$ according to Relation 21 and Relation 22:

$$M_Z = M_{D,t} - M_{NZ} \tag{21}$$

$$M_Z = M_{D,t} - SV_D(t_Z) \tag{22}$$

with $$V_D(t_Z) = V_{DO} - Qt_Z \tag{23}$$

when $V_{DO}$ is the original agent volume. From Relation 20 and Relation 22, $M_Z$ can be eliminated with $V_D(t_Z)$ substituted from Relation 23 to yield Relation 24:

$$t_Z = \frac{M_{D,t}\left(1 - \frac{S}{\rho}\right)}{Z - Q \cdot S} \tag{24}$$

Relation 16 and Relation 24 result in Relation 25 in which $t_Z$ is expressed independent of Q:

$$t_Z = \frac{M_{D,t}\left(1 - \frac{S}{\rho}\right)}{F_S \cdot S} = \frac{M_{D,t}}{\rho \cdot Q_M} \tag{25}$$

The result states that all osmotic systems constructed with two compartments containing the same agent with the same imbibition rate $F_S$ take substantially identical times for substantially all the agent in D compartment to dissolve; and, the effect or programming different Q's will be reflected in the magnitude of the zero order rate of release and the amount of agent delivered at zero time. The fraction of agent not delivered by the system at a zero order rate of release is given by Relation 26 wherein $M_{NZ}$ is the mass of agent not delivered at a zero order rate of release:

$$\frac{M_{NZ}}{M_{D,t}} = \frac{S}{M_{D,t}} V_d(t_Z) = \frac{S}{\rho} \frac{V_D(t_Z)}{V_{DO}} \tag{26}$$

and by substituting Relation 23 into Relation 26, the following Relation 27 and 28 obtained:

$$\frac{M_{NZ}}{M_{D,t}} = \frac{S}{\rho} \cdot \frac{V_{DO} - Qt_Z}{V_{DO}} \tag{27}$$

$$\frac{M_{NZ}}{M_{D,t}} = \frac{S}{\rho}\left[1 - \frac{Q_p}{F_S \cdot S}\left(1 - \frac{S}{\rho}\right)\right] \tag{28}$$

and substituting $Q_M$ from Relation 12, Relation 29 is obtained:

$$\frac{M_{NZ}}{M_{D,t}} = \frac{S}{\rho}\left[1 - \frac{Q}{Q_M}\right] \tag{29}$$

which means that when $Q = Q_M$ no non-zero order delivery occurs, and when $Q = Q$, the fraction of agent not delivered from compartment D at a zero order rate of release is equal to $S/\rho$. The amount of agent delivered at a zero order rate of release is then given by Relation 30:

$$\frac{M_Z}{M_{D,t}} = 1 - \frac{M_{NZ}}{M_{D,t}} = 1 - \frac{S}{\rho}\left(1 - \frac{Q}{Q_M}\right) \tag{30}$$

which can be expressed in simplified Relation 31, with Relation 31 identical to Relation 18 to give Relation 32:

$$\frac{M_Z}{M_{D,t}} = 1 - \frac{S}{\rho} + \frac{S}{\rho}\left(\frac{Q}{Q_m}\right) \tag{31}$$

$$\frac{Z}{Z_M} = \frac{M_Z}{M_{D,t}} \tag{32}$$

The delivery rate after all the solid agent present in compartment D has dissolved in fluid imbibed into the compartment will decline over time with the rate of delivery given by Equation 5 with $C(t)$ determined below. The mass of agent dissolved in compartment D is expressed by Relation 33 as follows:

$$M_D(t) = C(t) \cdot V_{D(t)} \tag{33}$$

such that Relation 34 holds:

$$\left(\frac{dm_D}{dt}\right)_{out} = -V_D \frac{dC}{dt} - C \cdot \frac{dV_D}{dt} \quad (34)$$

since $$V_D + V_O = V_{total} \quad (35)$$

and Q is expressed by Relation 36:

$$\frac{-dV_D}{dt} = \frac{dV_D}{dt} = Q \quad (36)$$

and by combining Relation 34 and Relation 36 into Relation 5, Relation 37 is derived as follows:

$$-V_D \frac{dC}{dt} + QC = QC + \left(\frac{dV}{dt}\right)_D \cdot C \quad (37)$$

and by adopting the notation given in Relation 1:

$$F = (F_S/S) \cdot C \quad (38)$$

in which $F_S$ is the volume uptake of the agent compartment D, when containing a saturated solution such that Relation 37 and Relation 38 results in Relation 39:

$$-V_D \frac{dC}{dt} = \frac{F_S}{S} \cdot C^2 \quad (40)$$

which can be integrated from $t_Z$ to $t$ as in Relation 40 when the concentration changes from S to C:

$$-\int_S^C \frac{dC}{C^2} = \frac{F_S}{S} \int_{t_Z}^t \frac{dt}{V_D(t)} \quad (40)$$

where $V_D(t)$ is obtained by integrating Relation 36 to yield Relations 41 and 42 as follows:

$$-\int_{t_Z}^t dt = \frac{1}{Q} \int_{V_{Dt_Z}}^{V_{Dt}} dV_D \quad (41)$$

$$V_D(t) = V_D(t_Z) - Q(t - t_Z) \quad (42)$$

with the compression of the agent compartment D, continuing until a final time $t_f$ when $F_D(t_f) = 0$ which holds in Relation 43 as follows:

$$t_f = \frac{V_D(t_Z) + Qt_Z}{Q} = \frac{V_{DO}}{Q} \quad (43)$$

Substituting Relation 42 into Relation 40 and integrating the combined relations, Relation 44 is obtained and simplified as Relation 45:

$$\frac{1}{C} - \frac{1}{S} = \frac{-F_S}{QS} \int_{t_Z}^t \frac{d[V_D(t_Z) - Q(t - t_Z)]}{V_D(t_Z) - Q(t - t_Z)} \quad (44)$$

$$\frac{1}{C} - \frac{1}{S} = \frac{-F_S}{QS} \ln \frac{V_D(t_Z) - Q(t - t_Z)}{V_D(t_Z)} \quad (45)$$

from which C(t), as mentioned supra is calculated according to Relation 46:

$$C(t) = \frac{S}{1 - \frac{F_S}{Q} \ln\left[1 - \frac{Q(t - t_Z)}{V_D(t_Z)}\right]} \quad (46)$$

with Relation 23 substituted in Relation 46 to give Relation 47 alternatively written as Relation 48:

$$C(t) = \frac{S}{1 - \frac{F_S}{Q} \ln \frac{V_{DO} - Qt}{V_{DO} - Qt_Z}} \quad (47)$$

$$C(t) = \frac{S}{1 - \frac{F_S}{Q} \ln \frac{V_D(t)}{V_D(t_Z)}} \quad (48)$$

The non-zero order delivery rate is then obtained from Relations 5, 38 and 48 and given by Relations 49 and 50 as follows $$\frac{dm}{dt} = \frac{F_S}{S} \cdot C^2 + QC \quad (49)$$

$$\frac{dm}{dt} = \frac{F_S \cdot S}{\left[1 - \frac{F_S}{Q} \ln \frac{V_D(t)}{V_D(t_Z)}\right]^2} + \frac{Q \cdot S}{\left[1 - \frac{F_S}{Q} \ln \frac{V_D(t)}{V_D(t_Z)}\right]} \quad (50)$$

This delivery rate profile expressed in Relation 50 continues until a time $t_f = V_{DO}/Q$ given by Relation 43 supra, with $V_D(t)$ given by Relation 51 and similarly Relation 52:

$$V_D(t) = V_{DO} - Qt \quad (51)$$

$$V_D(t_Z) = V_{DO} - Qt_Z \quad (52)$$

Substituting Relations 51 and 52 into Relation 50 and using the definition of $t_f$ of Relation 43, it mathematically follows for Relation 53 that:

$$\frac{dm}{dt} = \frac{F_S \cdot S}{\left[1 - \frac{F_S}{Q} \ln \frac{(1 - \frac{t}{t_f})}{1 - \frac{t_Z}{t_f}}\right]^2} + \frac{Q \cdot S}{\left[1 - \frac{F_S}{Q} \ln \frac{1 - \frac{t}{t_f}}{1 - \frac{t_Z}{t_f}}\right]} \quad (53)$$

Relation 53 can be further normalized by substituting $t_Z$ and $t_f$ from Relations 25 and 43 and $Z_M$ from Relation 14 to give Relation 54 as follows:

$$\frac{1}{Z_M}\left[\frac{dm}{dt}\right] = \frac{\frac{F_S}{Q_M} \cdot \frac{S}{\rho}}{\left[1 - \frac{F_S}{Q} \ln \frac{(1 - \frac{t}{t_f})}{(1 - \frac{Q}{Q_M})}\right]^2} + \quad (54)$$

-continued $$\cfrac{\cfrac{Q}{Q_M} \cdot \cfrac{S}{\rho}}{\left[1 - \cfrac{F_S}{Q} \ln \cfrac{(1 - \cfrac{t}{t_f})}{(1 - \cfrac{Q}{Q_M})}\right]}$$

which can be expressed in units of $t_Z$ as shown in Relation 55:

$$\frac{1}{Z_M}\left[\frac{dm}{dt}\right] = \cfrac{\cfrac{F_S}{Q_M} \cdot \cfrac{S}{\rho}}{\left[1 - \cfrac{F_S}{Q} \ln \cfrac{1 - \cfrac{t}{t_Z} \cdot \left[\cfrac{Q}{Q_M}\right]}{1 - \cfrac{Q}{Q_M}}\right]^2} + \cfrac{\cfrac{Q}{Q_M} \cdot \cfrac{Q}{\rho}}{\left[1 - \cfrac{F_S}{Q} \ln \cfrac{1 - \cfrac{t}{t_Z} \cdot \left[\cfrac{Q}{Q_M}\right]}{1 - \cfrac{Q}{Q_M}}\right]} \quad (55)$$

which above presentation demonstrates that the volume released from the system per unit time expressed as $(dm/dt)$, is related to the volume of fluid imbibed into the agent compartment D, in unit time expressed as $(dV/dt)_D$, and to the volume of fluid imbibed into the osmagent compartment O, in unit time expressed as $(dV/dt)_O$, which relations are illustrated in FIGS. 6, 7 and 8.

EXAMPLE 2

The procedure employed in this example uses the relations of Example 1. The osmotic system suitable for the purpose of this example is designed and structured as described in FIGS. 1A through 1F. The osmotic system of the example is defined by S, $\rho$, Q, $F_S$, $M_{D,t}$ when Relation 6 is satisfied, and for these parameters the osmotic system performance is described in terms of normalized quantities as follows:

$$\frac{S}{\rho}, \frac{Q}{Q_M}, \frac{F_S}{Q}, t_f = \frac{V_{DO}}{Q}$$

The maximum zero order rate $Z_M$ is $Z_M = \rho \cdot Q_M$; and $Q_M/F_S$ is equal to $(S/\rho)/(1 - S/\rho)$. The zero order rate $Z/Z_M$ is a linearly decreasing function of $S/\rho$ with slope $(1 - Q/Q_M)$ as defined by Relation 19:

$$\frac{Z}{Z_M} = 1 - \frac{S}{\rho}\left[1 - \frac{Q}{Q_M}\right] \quad (19)$$

with zero order time $t_Z$ defined by Relation 25:

$$t_Z = \cfrac{M_{D,t}\left(1 - \cfrac{S}{\rho}\right)}{F_S \cdot S} = \cfrac{M_{D,t}}{\rho \cdot Q_M} \quad (25)$$

The fraction of agent delivered at zero order $M_Z/M_{Dt}$ also is a linearly decreasing function of $S/\rho$ and it is identical to Relation 19 and defined by Relation 30:

$$\frac{M_Z}{M_{D,t}} = 1 - \frac{M_{NZ}}{M_{D,t}} = 1 - \frac{S}{\rho}\left(1 - \frac{Q}{Q_M}\right) \quad (30)$$

The non-zero order delivery rate is given by Relation 54 or by Relation 55 as a function of time in units of $t_Z$.

According to the example, a dual compartment osmotic system comprising an agent compartment D, and an osmagent compartment O, or driving compartment is designed and structured to serve the agent compartment. When the imbibition flux of the agent compartment is designed at $F_S$ for any agent characterized by S and $\rho$, then the maximum driving rate $Q_M$ for the osmagent compartment is given by Relation 12 as plotted in FIG. 6. When the osmagent compartment is designed with inhibition flux $Q_M$, the osmotic system delivery profile will be substantially perfect zero order at all times at delivery rate $Z_M$ for a time $t_Z$ as shown by the square box in FIG. 7, wherein curve A represents $Q/Q_M = 0.5$, with $S/\rho = 0.3$, and curve B represents $Q/Q_M = 0.8$, with $S/\rho = 0.75$. The quantity $Z_M$ is given by Relations 12 and 14 and the quantity $t_Z$ is given by Relation 25.

For this system, when the imbibition rate of the osmotic compartment is Q and smaller than $Q_M$, the zero order time will still be $t_Z$ independent of Q. The zero order rate of release Z in this case will be a fraction of $Z_M$ as given by Relation 19. Also, the mass of agent delivered at zero order $M_Z$ will be an identical fraction of the total agent mass delivered according to Relation 30 as shown in FIG. 8. The design of an osmotic system according to this example will only be necessary for agents with an $S/\rho > 0.2$. With a dual osmotic system, it is necessary that $M_Z/M_{Dt} \geq 0.8$ to obtain an optimum dosage form index or minimum plasma concentration fluctuation. This delivery parameter can be programmed with the dual compartment system and it is the area in FIG. 8 in the right hand upper quadrant indicated by dashed vertical lines parallel to the ordinate at 0.2 on the abscissa, at 0.8 on ordinate, and with an upper limit of 1.0. This area contains the values of $Q/Q_M$ which can be programmed as indicated by $S/\rho$ values. The fractional amount of agent which is not delivered during the time $t_Z$ because $Q < Q_M$, is delivered in a non-zero order manner. Two additional examples are considered for which 85% of the agent is delivered at zero order $Z/Z_M = 0.85$ are plotted in FIG. 7, these are identified as curves A and B. For A, when $S/\rho = 0.3$ then $Q/Q_M = 0.5$ and the zero order rate of release is then $Z = 0.85\, Z_M$. The non-zero order rate of release is calculated from Relation 55 with $Q_M/F_S = 0.0428$ as read from FIG. 6. Thus, for these conditions the calculations are as follows:

$$\frac{F_S}{Q} = \frac{F_S}{Q_M} \cdot \frac{Q_M}{Q} = \frac{1}{0.428} \times \frac{1}{0.5} = 4.67,$$

$$\frac{Q}{Q_M} \cdot \frac{S}{\rho} = 0.5 \times 0.3 = 0.15,$$

$$\frac{F_S}{Q_M} \cdot \frac{S}{\rho} = \frac{1}{0.428} \times \frac{0.3}{1} = 0.701,$$

with the final time $t_f = Q_M/Q \cdot t_Z = 2 \cdot t_Z$, and the non-zero order rate of release for this system given according to Relation 55 as follows:

$$\frac{1}{Z} \cdot \frac{1}{dt} = \frac{0.7}{\left[1 - 4.67 \ln \frac{(1 - \frac{t}{t_z} \times 0.5)}{0.5}\right]^2} +$$

$$\frac{0.15}{\left[1 - 4.67 \ln \frac{(1 - 0.5 \frac{t}{t_z})}{0.5}\right]}$$

with the numerical values obtained listed in Table I and plotted in FIG. 7 as curve A. In Table I, $t/t_Z$ is the time the osmotic system delivers at zero order and $1/Z(dm/dt)$ is the non-zero order rate of release of agent delivered from the osmotic system given as a fraction of the zero order rate of release of agent delivered from the osmotic system.

TABLE I

| $t/t_Z$ | $1/Z(dm/dt)$ |
|---|---|
| 1.00 | 0.850 |
| 1.05 | 0.577 |
| 1.10 | 0.414 |
| 1.25 | 0.187 |
| 1.50 | 0.07 |
| 1.75 | 0.03 |

For B, $Z/Z_M = 0.85$, $S/\rho = 0.75$, and $Q/Q_M = 0.8$ as seen in FIG. 8. For these conditions additional characteric numbers are as follows:

$$\frac{F_S}{Q} = \frac{1}{3} \times \frac{1}{0.8} = 0.417,$$

$$\frac{Q}{Q_M} \cdot \frac{S}{\rho} = 0.8 \times 0.75 = 0.60,$$

$$\frac{F_S}{Q_M} \cdot \frac{S}{\rho} = \frac{1}{3} \times 0.75 = 0.25,$$

$$t_f = \frac{Q_M}{Q} \cdot t_Z = \frac{1}{0.8} t_Z = 1.25 t_Z,$$

with the numerical values obtained listed in Table II and plotted in FIG. 7 as curve B. The expressions $t/t_Z$ and $1/Z(dm/dt)$ in Table II are as defined for Table I:

TABLE II

| $t/t_Z$ | $1/Z(dm/dt)$ |
|---|---|
| 1.00 | 0.85 |
| 1.10 | 0.66 |
| 1.20 | 0.45 |
| 1.23 | 0.35 |
| 1.24 | 0.30 |
| 1.25 | 0.20 |

In A and B the zero order rate of release is identical at 0.85 $Z_M$. The non-zero order rate for each case has a $$\int_{t_Z}^{t_f} \frac{dm}{dt} \cdot dt = M_{NZ} = 0.15 M_{Dt}$$

different time dependency but the mass of drug not delivered at zero order is $M_{NZ}$ as given by the integral for each case. For A where the first term in Relation 55 is dominant, the curve is concaved upward, and for B where the second term is dominant, the curve is convexed upward. Thus, since the osmotic systems are designed with $Z/Z_M > 0.8$, the time dependency of the negligible tail is of little consequence.

EXAMPLE 3

An osmotic therapeutic system manufactured in the form of an oral, osmotic device for delivering the antiarrhythmic and antifibrillatory drug procainamide hydrochloride to the gastointestinal tract was manufactured as follows: first, 225 mg of procainamide hydrochloride was pressed into a solid mass in a commercially available Manesty tableting machine to a Stoke's hardness of 8 kg. Next, the solid was coated in a standard air suspension machine with a semipermeable polymeric expandable film formed from a 5% solution consisting of cellulose acetate having an acetyl content of 32%. The solution was made by dissolving 155 g of cellulose acetate in a solvent consisting of 3300 ml of acetone and 330 ml of water. The acetone and water had a 88.5 to 11.5 weight to weight basis. The freshly formed film had a thickness of 5 mils.

Next, 350 mg of the osmagent sodium chloride was pressed in the Manesty machine to a Stoke's hardness of 8 kg. The pressed sodium chloride had a shape identical to the shape of the pressed procainamide hydrochloride. Then, a small drop of liquid cellulose acetate was spread onto one surface of the pressed sodium chloride and this surface was placed against a corresponding surface of the film coated procainamide hydrochloride. The two united masses were then coated in the air suspension machine with a wall of semipermeable cellulose acetate to a thickness of 10.0 mils. The wall was formed using the polymeric solution prepared immediately above. Finally, an osmotic passageway having a diameter of 10 mils was drilled through one wall facing the procainamide hydrochloride for delivering it from the system.

The procainamide hydrochloride used in this system had a $S/\rho$ value of 0.8. For this system containing 225 mg of procainamide hydrochloride the minimum amount of sodium chloride required for delivering the procainamide hydrochloride was obtained from Relation 6 wherein $S_D$ is the solubility of sodium chloride, $M_D$ is the amount of procainamide hydrochloride, $\rho_D$ is the density of procainamide hydrochloride, and $\rho_O$ is the density of NaCl.

$$(M_O)_{min} = \frac{S_D \cdot M_D \cdot /\rho_D}{(1 - S_O/\rho_O)}$$

$$= \frac{(320)(255)(1000)}{(1 - 320/1540)}$$

$$= 130 \text{ mg}$$

Figure 9:
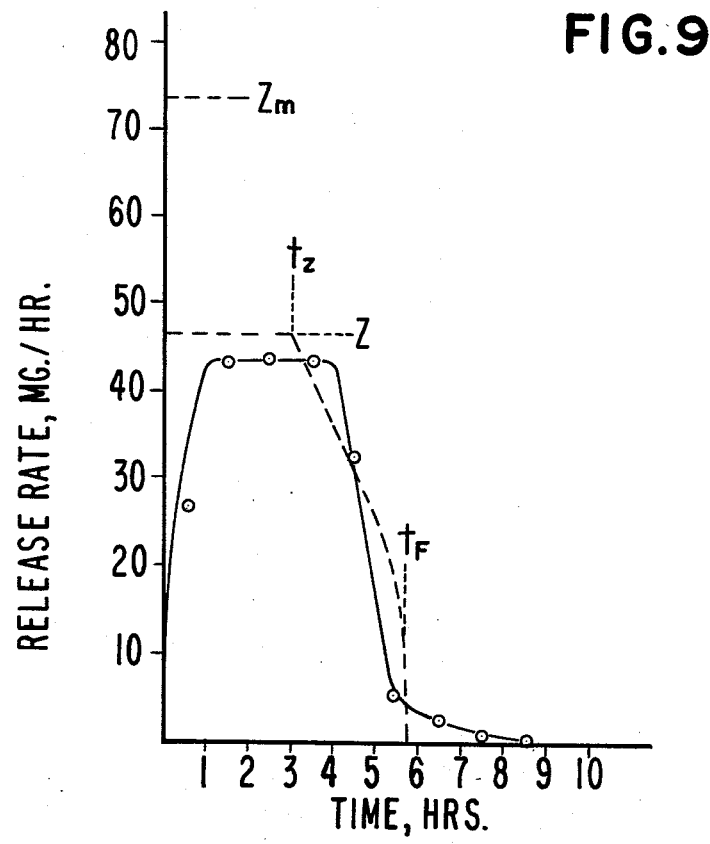
FIG. 9 is a graph indicating the actual amount of agent released from an osmotic system compared with the theoretical amount of agent released from the system.

For the system just manufactured $Q < Q_M$ since $F/S > \rho/S = 1$, where $k\pi_D$ is the water transmission rate into the agent compartment, $k\pi_O$ is the water transmission rate into the osmagent compartment:

$$\frac{(k\pi)_D A_D/h_D}{(k\pi)_o A_o/h_o} > \frac{\rho}{S} - 1$$

$$\frac{(0.154)(1.8)/15}{(0.26)(1.5)/10} > \frac{1000}{800} - 1$$

wherein the value obtained $0.47 > 0.25$ indicates that the system delivery rate is functioning at a level less than its maximum rate of release as seen in FIG. 9 where the maximum zero order rate is $Z_M$. Further, from Relation 16:

$$Z = (F_S = Q) \cdot S$$

$$= ([k\pi]_D A/h_D + [k\pi]_O A/h_O) \cdot S$$

$$= (0.0185 + 0.0396) \cdot 800$$

$$= 46.5 \text{ mg/hr,}$$

which is the system's zero order rate of release which is indicated in FIG. 9 as Z; also, from Relation 13:

$$Z_M = \frac{F_S \cdot S}{1 - \frac{S}{\rho}} = \frac{(0.0185)(800)}{1 - \frac{800}{1000}} = 74 \text{ mg/hr,}$$

which is the maximum delivery rate $Z_M$ as seen in FIG. 9 along the ordinate, and from Relation 25:

$$t_Z = M_t/Z_M$$

$$= (225)/74$$

$$= 3.0 \text{ hr.}$$

which is the time the system theoretically delivers the maximum amount at a zero order rate of release; and from Relation 43:

$$t_f = \frac{\left(\frac{M_D}{\rho}\right)}{Q} = \frac{\left(\frac{225}{1000}\right)}{0.0396} = 5.7 \text{ hr.}$$

which is the time all the agent is expected to be delivered from the system; and wherein the non-zero order rate of release is as follows:

$$\frac{dm}{dt} = \frac{F_S \cdot S}{\left[1 - \frac{F_S}{Q} \ln \frac{(1 - \frac{t}{t_f})}{1 - \frac{t_z}{t_f}}\right]^2} +$$

$$\frac{Q \cdot S}{\left[1 - \frac{F_S}{Q} \ln \frac{1 - \frac{t}{t_f}}{1 - \frac{t_z}{t_f}}\right]}$$

$$\frac{dm}{dt} = \frac{14.8}{\left[1 - 0.467 \ln \frac{1 - \frac{t}{5.7}}{0.474}\right]^2} +$$

$$\frac{31.7}{\left[1 - 0.467 \ln \frac{1 - \frac{t}{5.7}}{0.474}\right]}$$

wherein $dm/dt$ is plotted in FIG. 9 as the non-zero order rate of release indicated by the dashed line.

In FIG. 9 the actual amount of procainamide hydrochloride released from the system was measured and plotted against the calculated amount released over a prolonged period of time. The line with the circles represents the actual amount released and the dashed lines represents the calculated release. The system actually released 70% of its procainamide hydrochloride against an expected release of 62%.

EXAMPLE 4

Figure 10:
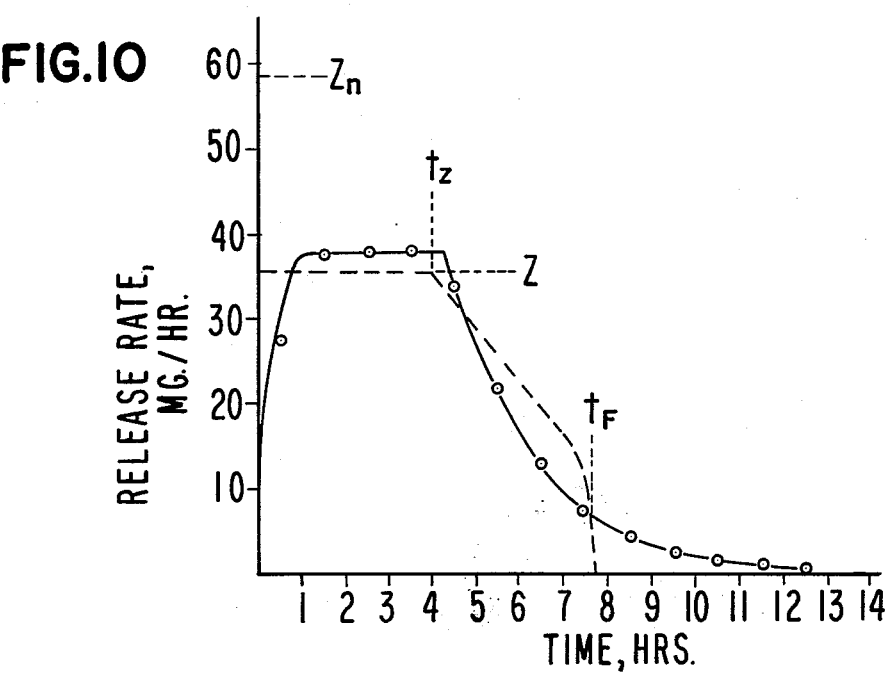
FIG. 10 is similar to FIG. 9 and it shows the actual amount of agent released compared with the theoretical amount released from a system made with a wall and a film having a different thickness than the system of FIG. 9.

An osmotic, therapeutic system was manufactured in the form of an oral, osmotic device by following the procedure of Example 3, with all conditions and procedures as described, except the film had a thickness of 7.5 mils and the wall has a thickness of 7.5 mils. For this system $F_S/Q > \rho/S - 1$ or $0.50 > 0.25$. Repeating the calculations of Example 3, the following values are obtained: $Z = 35.2$ mg/hr; $Z_M = 58.8$ mg/hr; $t_Z = 3.8$ hrs.; and $t_f = 7.7$ hrs. The interpretation of Z, $Z_M$, $t_Z$ and $t_F$ is as in FIG. 3. The non-zero order rate of release is given by the following:

$$\frac{dm}{dt} = \frac{11.76}{\left[1 - 0.502 \ln \frac{1 - \frac{t}{7.7}}{0.506}\right]^2} +$$

$$\frac{23.44}{\left[1 - 0.502 \ln \frac{1 - \frac{t}{7.7}}{0.506}\right]}$$

wherein $dm/dt$ is plotted in FIG. 10 as the non-zero order rate of release indicated by the dashed line.

In FIG. 10, the actual amount of procainamide hydrochloride released from the system of Example 4 was measured and plotted against the calculated amount released over a prolonged period of time. The line with the circles represents the actual amount released, and the dashed lines represent the calculated release. The system actually released 62% of its procainamide hydrochloride at constant rate and it had a calculated percentage of 59%.

EXAMPLE 5

The procedures of Examples 3 and 4 are repreated in this example with all conditions as previously described except that the agent in the agent compartment is replaced with a member selected from the group consisting of hypnotics, sedatives, psychic energizers, tranquilizers, anticonvulsants, muscle relaxants, antiparkinson agents analgesics, anti-inflammatory, anesthetics, muscle contractants, anti-microbials, antimalarials, hormones, sympathomimetics, diuretics, hypoglycemics, and nutritional agents.

EXAMPLE 6

The procedures of Examples 3, 4 and 5 are repeated in this example, with all conditions as described except that the agent in the agent compartment is replaced with a member selected from the group consisting of prochlorperazine edisylate, ferrous sulfate, aminocaproic acid, potassium chloride, mecamylamine hydrochloride, amphetamine sulfate, benzphetamine hydrochloride, isoproternol sulfate, methamphetamine hydrochloride, phenmetrazine hydrochloride, bethanechol chloride, methacholine chloride, atropine sulfate, methscopolamine bromide, isopropamide iodide, tridihexethyl chloride, phenformin hydrochloride, and methylpehnidate hydrochloride.

EXAMPLE 7

The procedures of Example 3 and 4 are repeated in this example with all conditions as previously described except that the system is designed as an ocular, osmotic therapeutic system and the agent compartment contains an ophthalmic drug that is a member selected from the group consisting of idoxuridine, phenylephrine, pilocarpine hydrochloride, eserine, carbachol, phospholine iodine, demecarium bromide, cyclopentolate, homatropine, scopolamine and epinephrine.

EXAMPLE 8

Figure 11A:
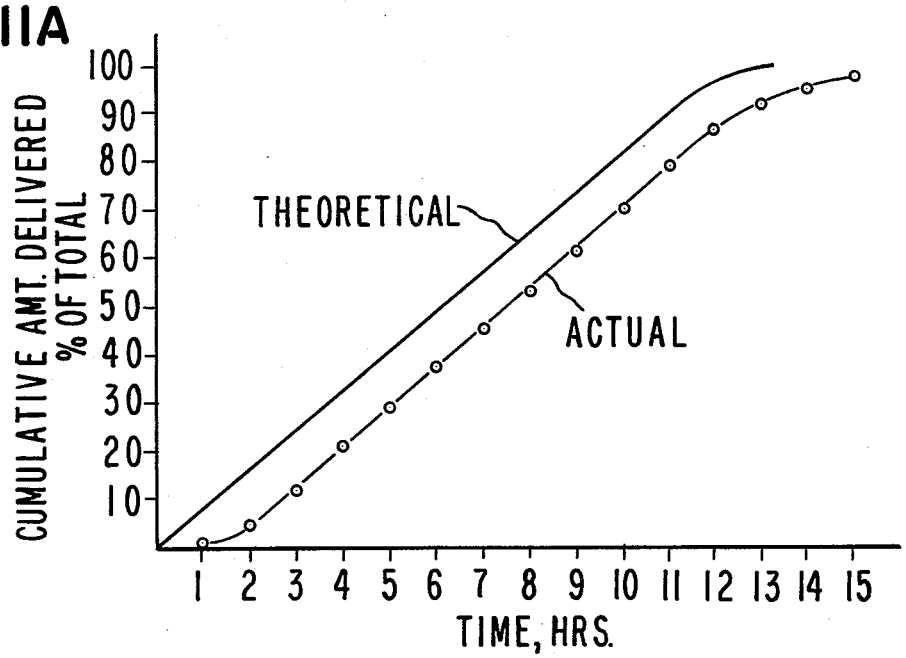
FIGS. 11A and 11B represent the actual and theoretical rates of release for an osmotic system having an expandable film made from a polymeric material containing a film expanding agent.
Figure 11B:
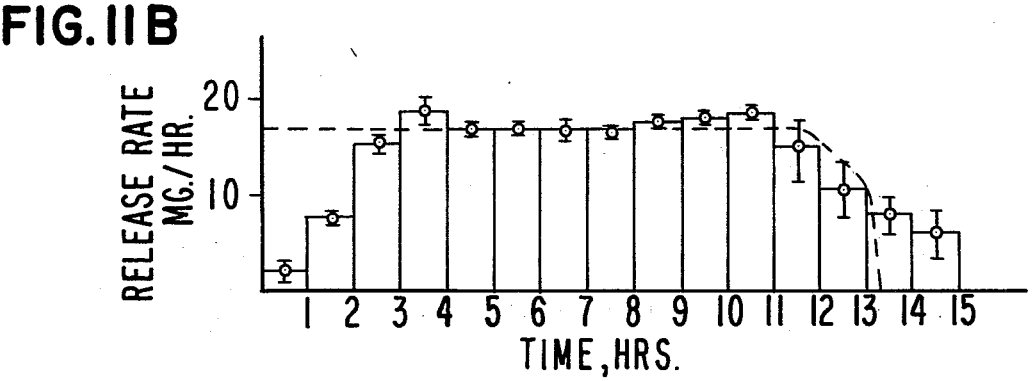

In this example, an oral osmotic therapeutic system was manufactured according to the procedures of Examples 3 and 4. The procainamide hydrochloride of the example was coated with a 3.0 mil thick semipermeable polymeric expandable film formed from a 5% solution consisting of 70% cellulose acetate having an acetyl content of 38.3%, and 30%, and 30% polyethylene glycol having a molecular weight of 400 dissolved in a 80 to 20 parts by weight of methylene chloride methanol solvent, and then bonded to a press mass of osmagent ammonium chloride. The two components were finally coated with the cellulose acetate solution of Example 3 to form an exterior wall having a thickness of 3.6 mils. The theoretical rate of release and the actual rate of release for this system are presented in FIGS. 11A and 11B. In the figures, the dashed lines represent the theoretical and the line with the circles represent the actual rate of release. The system had a measured rate of release of 17 mg per hour for 11 hours as released through a passageway having a diameter of 8.7 mils. This system released 80% of the agent at a zero order rate of release.

EXAMPLE 9

The procedure of Example 8 is followed in this example with the manufacturing steps as described. In this example, the osmagent ammonium chloride is pressed and coated with the expandable film forming solution consisting of 70% cellulose acetate having an acetyl content of 38.3% and 30% polyethylene glycol 400 as prepared in Example 8. The agent of the system is pressed into a correspondingly shaped configuration with the agent selected from the group of agents having limited solubility that can be delivered by the system including diphenidol, meclizine hydrochloride, prochlorperazine maleate, thiethylperpazine maleate, anisindione, dipenadione, erythrityl tetranitrate, digoxin, isofurophate, reserpine, acetazolamide, methazolamide, bendroflumethrazide, allopurinol and aspirin. The insoluble agent is admixed with an equal part of sorbitol containing methyl cellulose as a binder and suspending agent. The two components are adhesively bound and a wall of cellulose acetate having an acetyl content of 32% is applied as described in Example 8. The passageway communicating with the exterior of the system and the agent compartment has a diameter of 8.7 mils.

EXAMPLE 10

Figure 12A:
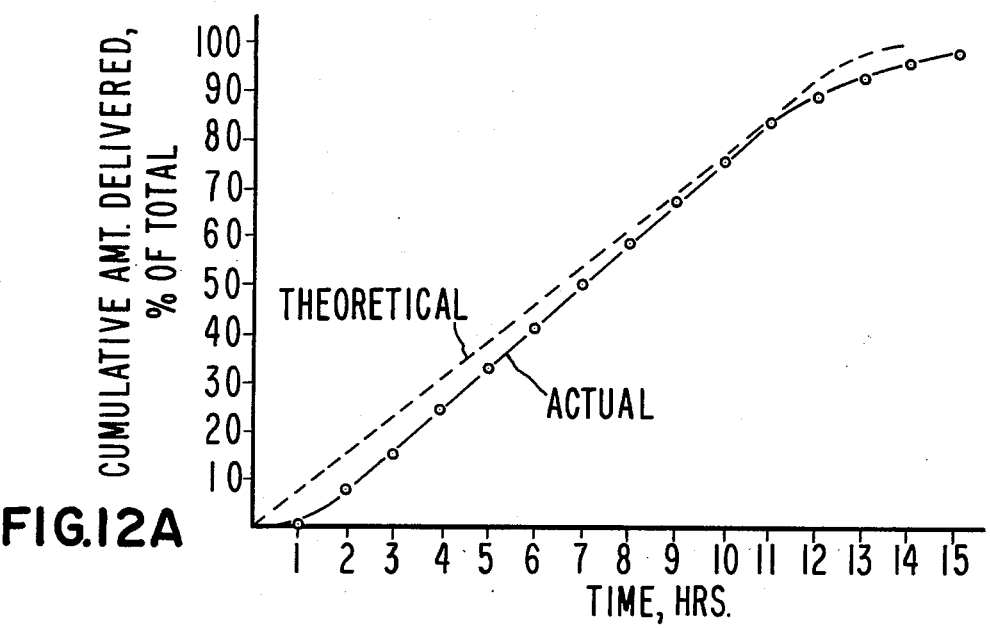
FIGS. 12A and 12B represent the actual and theoretical rates of release achieved for an osmotic system having a different osmagent as the driving force; and, FIG. 13 is a graph indicating the actual rates of release for three osmotic systems, each having a progressively thicker wall.
Figure 12B:
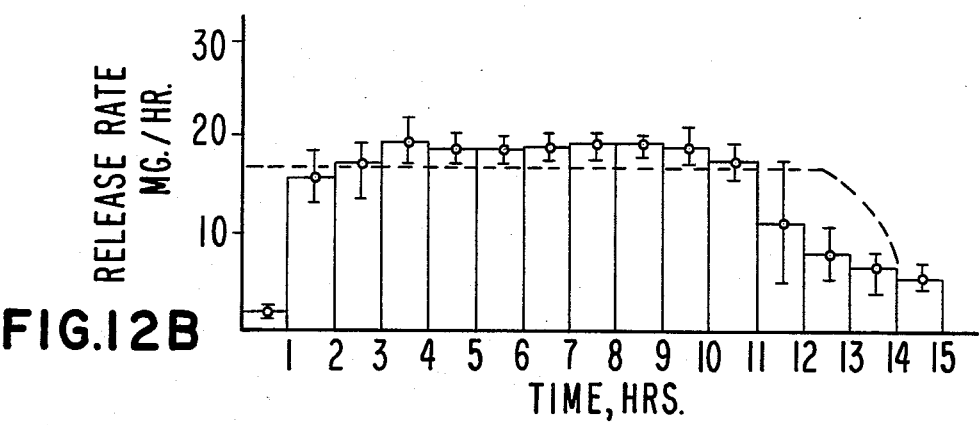

The procedure of Example 8 was followed in this example with all conditions as described except the osmagent in this example was sorbitol. The theoretical rate of release and the actual rate of release for this system are presented in FIGS. 12A and 13B. In the figures, the dashed lines represent the theoretical and the lines with the circles represent the actual rate of release. The system had a measured rate of release of 17 mg per hour for 12 hours. The passageway had a diameter of 8.7 mils. This system released 75 to 85% of the agent at a zero order rate of release.

EXAMPLE 11

The procedure of Example 9 is repeated in this example and all manufacturing conditions are as described, except the osmagent is a mixture of ammonium chloride and sodium chloride.

EXAMPLES 12 to 14

Three dual compartment osmotic devices were prepared according to the procedures of Examples 3 and 8. The agent compartment in the three devices contained procainamide hydrochloride and the osmagent compartment contained ammonium chloride. The film surrounding the osmagent was 5 mils thick and it consisted of cellulose acetate having an acetyl content of 36.4% produced by blending cellulose acetate having an acetyl content of 32% with cellulose acetate having an acetyl content of 39.8% in acetone and water. The two compartments were attached with a water soluble paste. The wall surrounding the compartments consisted of cellulose acetate having an acetyl content of 34.5%. The release parameters for the three systems are listed in Table III.

TABLE III

| Eg. | Wall Thickness Mils | Z (mg/hr) | $t_Z$ (hr) | $t_T$ (hr) | % Delivered at Zero Order | Flux Ratio |
|---|---|---|---|---|---|---|
| 12 | 4 | 50 | 4.3 | 4.3 | 100 | 0.19 |
| 13 | 6 | 43 | 5.0 | 5.0 | 100 | 0.25 |
| 14 | 8 | 33 | 5.8 | 7.0 | 89 | 0.29 |

Figure 13:
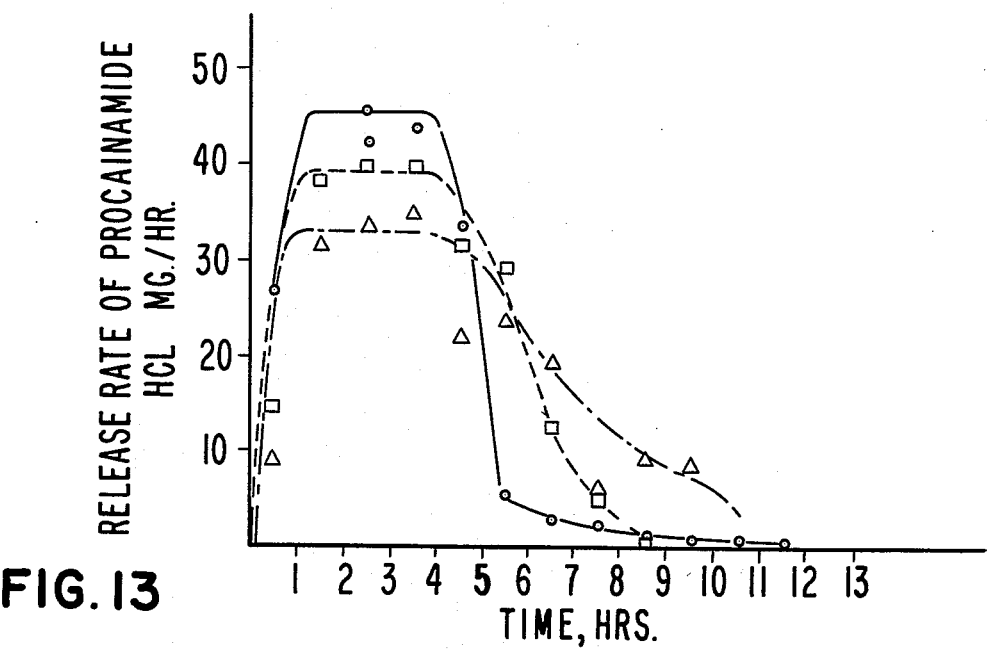

In Table III, Eg. is example, Z is the zero order rate of agent release, $t_Z$ is the time in hours the system delivered at zero order rate of release, $t_T$ is the total time the system delivered agent, and Flux Ratio is $F_S/Q$. The systems contained 215 mg of procainamide hydrochloride and 325 mg of ammonium chloride. The passageways in the systems had a diameter of 10 mils. The actual delivery of agent from these systems is plotted in FIG. 13. In FIG. 13, the line with the circles is Example 12, the line with the squares is Example 13 and the line with the triangles is Example 14.

The novel osmotic systems of this invention use means for the obtainment of precise release rates in the environment of use while simultaneously maintaining the integrity and character of the system. While there has been described and pointed out features of the invention as applied to presently preferred embodiments, those skilled in the art will appreciate that various modifications, changes, additions and omissions in the systems illustrated and described can be made without departing from the spirit of the invention.

I claim:

1. An osmotic therapeutic system for the controlled delivery of a beneficial drug to a biological environment, comprising:
   a. a wall formed of a semipermeable material permeable to the passage of external fluid present in the environment and substantially impermeable to the passage of drugs and compounds; the semipermeable wall surrounding and forming;
   b. a first and second compartment, said first compartment containing a drug that is in direct communication with the semipermeable wall, said second compartment containing an osmotically effective compound that exhibits an osmotic pressure gradient across the semipermeable wall against the fluid, with the compartments separated by a flexible membrane, which membrane is substantially impermeable to the passage of drug, compound and fluid;

c. a passageway in the wall communicating with the compartment containing the drug for delivering drug from the system; and, d. wherein in operation when the system is in the environment of use, fluid from the environment is imbibed through the wall into (1) the first compartment containing drug in a tendency towards osmotic equilibrium at a rate determined by the permeability of the wall and the osmotic pressure gradient across the wall thereby forming a formulation containing drug, and into (2) the second compartment containing osmotic compound in a tendency towards osmotic equilibrium at a rate determined by the permeability of the wall and the osmotic pressure gradient across the wall thereby continuously filling the second compartment and expanding the membrane into the first compartment, whereby, through the combined actions of the first and second compartments, drug is delivered through the passageway from the system at a controlled rate over a prolonged period of time.

2. The osmotic therapeutic system for the controlled delivery of the beneficial drug according to claim 1, wherein the drug is a member selected from the group consisting of anticonvulsant, antiparkinson, analgesic, anti-inflammatory, anesthetic, hormonal, contraceptive, sympathomimetic, diuretic, ophthalmic, central nervous system, sedative, tranquilizer, anti-infective and hypoglycemic drugs.

3. The osmotic therapeutic system for the delivery of the beneficial drug according to claim 1, wherein the system is sized, shaped and adapted as a dosage form for delivering drug to the anal tract.

4. The osmotic therapeutic system for the delivery of drug according to claim 1, wherin the drug is a member selected from the group of drugs that have limited solubility in the fluid and exhibits a limited osmotic pressure gradient across the wall against the fluid, and drugs that are practically insoluble in the external fluid.

5. The osmotic therapeutic system for the delivery of the drug according to claim 1, wherein the compartment containing the drug also contains a compound that is soluble in the external fluid and exhibits an osmotic pressure gradient across the wall against the fluid.

6. The osmotic system for the controlled and continuous delivery of the beneficial drug according to claim 1, wherein the system is sized, shaped and adapted as a dosage form for delivering drug to the gastrointestinal tract.

7. The osmotic system for the controlled and continuous delivery of the drug according to claim 1, wherein the fluid imbibed into the second compartment containing the osmotic compound, dissolves the compound and increases the volume of said second compartment urging it to expand the membrane against the first compartment and correspondingly decrease the volume of the first compartment.

8. The osmotic system for the controlled and continuous delivery of the beneficial drug according to claim 1, wherein the fluid imbibed into the second compartment containing the osmotic compound increases the volume of the second compartment and expands the membrane into the drug compartment thereby concentrating the drug in the drug compartment.

9. An osmotic system for the controlled and continuous delivery of a beneficial agent to the environment of use comprising:

a. a shaped wall formed of a semipermeable material permeable to the passage of an external fluid in the environment of use and substantially impermeable to the passage of beneficial agent and compound, the shaped semipermeable wall surrounding and forming;

b. a first and second compartment, said compartments separated by an expandable membrane permeable to fluid and substantially impermeable to beneficial agent and compound, and wherein the first compartment contains a beneficial agent in communication with the semipermeable wall and the second compartment contains an osmotically effective compound that exhibits an osmotic pressure gradient directly across the semipermeable wall against the fluid;

c. a passageway in the semipermeable wall communicating with the beneficial agent compartment and the exterior of the system for delivering the beneficial agent from the system; and, d. wherein in operation, when the system is in the environment of use, fluid from the environment is imbibed through the semipermeable wall into (1) the first compartment containing the beneficial agent in a tendency towards osmotic equilibrium at a rate determined by the permeability of the wall and the osmotic pressure gradient across the wall, and into (2) the second comparment containing osmotically effective compound through the membrane at a rate determined by the permeability of the membrane and the osmotic pressure gradient across the membrane, said imbibitions increasing the volume of the second compartment and expanding the membrane into the compartment containing beneficial agent is delivered through the passageway from the system at a controlled rate over a prolonged period of time.

10. The osmotic system for the controlled and continuous delivery of the beneficial agent according to claim 9, wherein the beneficial agent is a member selected from the group consisting of an agent having limited solubility in the fluid and an agent that is practically insoluble in the fluid, and wherein said agents are mixed with an osmotically effective compound that is soluble in the fluid and exhibits an osmotic pressure gradient across the semipermeable wall against the fluid.

11. The osmotic system for the controlled and continuous delivery of beneficial agent according to claim 9, wherein the membrane is formed integral with the compartment containing the beneficial agent and serves as a wall of the compartment containing the osmotic compound.

12. The osmotic system for the controlled and continuous delivery of beneficial agent according to claim 9, wherein the membrane is formed integral with the compartment containing the osmotic compound and serves as a wall of the compartment containing the beneficial agent.

13. The osmotic system for the controlled and continuous delivery of the beneficial agent according to claim 9, wherein the beneficial agent is soluble to very soluble in the fluid and exhibits an osmotic pressure gradient across the wall against the fluid.

14. The osmotic system for the controlled and continuous delivery of the beneficial agent according to claim 9, wherein the system is sized, shaped and adapted for administering the beneficial agent to the gastrointestinal tract.

15. The osmotic system for the controlled and continuous delivery of the beneficial agent according to claim 9, wherein the semipermeable wall is formed of a member selected from the group of semipermeable materials consisting of cellulose acetate, cellulose diacetate, cellulose triacetate, polyurethane, polyamide, sulfonated polystyrene, cellulose acetate valerate, and cellulose acetate succinate.

16. The osmotic system for the controlled and continuous delivery of the beneficial agent according to claim 9, wherein the membrane contains from 0.01% to 40% of a member selected from the group consisting of polyalkylene glycol, preferably polyethylene glycol having a molecular weight of 300 to 6,000 of the formula H—(—OCH$_2$CH$_2$)$_n$—OH wherein $n$ is 5 to 204; poly($\alpha,\omega$)-alkylenediols; polyester alkylene glycol; and mixtures thereof.

17. The osmotic system for the controlled and continuous delivery of the beneficial agent according to claim 9, wherein the semipermeable wall is thicker than the membrane and imbibition of fluid by the osmotically effective compound is accompanied by an expansion of the membrane as fluid continuously fills the osmotic compound compartment and exerts force against the membrane.

18. The osmotic system for the controlled and continuous delivery of the beneficial agent according to claim 9, wherein the membrane surrounds the compartment containing the beneficial agent and has a surface adjacent to the compartment containing the osmotic compound, and wherein the membrane is formed of a material permeable to the passage of fluid, impermeable to the passage of beneficial agent and osmotic compound, and is movable from an original position to an expanded position.

19. The osmotic system for the controlled and continuous delivery of the beneficial agent according to claim 9, wherein the membrane surrounds the compartment containing the osmotic compound and has a surface adjacent to the compartment containing the beneficial agent, and wherein the membrane is formed of a material permeable to the passage of fluid, impermeable to the passage of beneficial agent and osmotic compound, and is movable from an original position to an expanded position.

20. The osmotic system for the controlled and continuous delivery of the beneficial agent according to claim 9, wherein the membrane is positioned between the beneficial agent and the osmotic compound compartments, and wherein the membrane contains an expansion agent that imparts flexibility and expandability to the membrane and is selected from the group consisting of phthalates, phosphates, citrates, adipates, tartrates, sebacates, succinates, glycolates, glycerolates, benzoates, and myristates.

21. The osmotic system for the controlled and continuous delivery of the beneficial agent according to claim 9, wherein the beneficial agent is a member selected from the group consisting of pesticides, herbicides, germicides, fungicides, insecticides and algicides.

22. An osmotic system sized, shaped and adapted for placement in an environment of use, comprising:
 a. a shaped wall formed of a non-toxic semipermeable material permeable to the passage of fluid present in the environment of use and substantially impermeable to the passage of beneficial agent and osmotically effective agent;
 b. the semipermeable wall surrounding and forming a compartment housing a membrane that divides the compartment into an area containing beneficial agent in contact with the semipermeable wall and an area containing an osmotically effective agent in contact with the semipermeable wall;
 c. a passageway in the wall communicating with the area containing the beneficial agent for delivering said beneficial agent from the system; and,
 d. wherein in operation, when the system is in the environment, fluid is imbibed through the semipermeable wall into the areas in a tendency towards osmotic equilibrium at a rate determined by the permeability of the semipermeable wall and the osmotic pressure gradient across the semipermeable wall thereby delivering beneficial agent through the passageway from the system, with the amount of beneficial agent delivered from the system related to the volume of fluid imbibed into the area containing the beneficial agent and the volume of fluid imbibed into the area containing the osmotically effective agent over a prolonged period of time.

23. The osmotic system sized, shaped and adapted for placement in an environment of use according to claim 22, wherein as the area containing the osmotic agent continuously increases in volume, the area containing the beneficial agent correspondingly diminishes in volume, and wherein the beneficial agent is a drug which is delivered from the system at a controlled rate over a prolonged period of time.

24. The osmotic system sized, shaped and adapted for placement in an environment of use according to claim 22, wherein the beneficial agent is present in the area as a solid, gel, paste, semisolid, cream or emulsion, which beneficial agent is mixed with fluid imbibed into the area for delivery through the passageway from the area at a controlled rate over a prolonged period of time.

25. The osmotic system for placement in the environment according to claim 22, wherein the beneficial agent exhibits a solubility of from practically insoluble to very soluble in the fluid and is mixed with an osmotically effective agent that exhibits an osmotic pressure gradient across the semipermeable wall against the fluid.

26. The osmotic system for placement in the environment according to claim 22, wherein the environment is a biological environment and the beneficial agent is a member selected from the group consisting of corticosteroids, androgens, estrogens and progestational steroids.

* * * * *